US012667617B2

(12) United States Patent
Johnson et al.

(10) Patent No.: US 12,667,617 B2
(45) Date of Patent: *Jun. 30, 2026

(54) CANCER TREATMENT DELIVERY COMPONENT INCLUDING A CARBON-BASED NANOMATERIAL COMPOSITION, METHOD OF DELIVERING A CANCER TREATMENT DELIVERY COMPONENT INCLUDING A CARBON-BASED NANOMATERIAL COMPOSITION, AND METHODS OF FORMING THE SAME

(71) Applicant: NABORS ENERGY TRANSITION SOLUTIONS LLC, Houston, TX (US)

(72) Inventors: Evan Johnson, Spring, TX (US); Anthony G. Petrello, Houston, TX (US); Paul Yollin, Tomball, TX (US); Dylan Cook, Spring, TX (US)

(73) Assignee: NABORS ENERGY TRANSITION SOLUTIONS LLC, Houston, TX (US)

( * ) Notice: Subject to any disclaimer, the term of this patent is extended or adjusted under 35 U.S.C. 154(b) by 275 days.

This patent is subject to a terminal disclaimer.

(21) Appl. No.: 18/529,658

(22) Filed: Dec. 5, 2023

(65) Prior Publication Data

US 2024/0181060 A1 Jun. 6, 2024

Related U.S. Application Data

(60) Provisional application No. 63/386,210, filed on Dec. 6, 2022.

(51) Int. Cl.
*A61K 41/00* (2020.01)
*A61K 47/52* (2017.01)

(52) U.S. Cl.
CPC .......... *A61K 41/0028* (2013.01); *A61K 47/52* (2017.08)

(58) Field of Classification Search
CPC ............................ A61K 41/0028; A61K 47/52
See application file for complete search history.

(56) References Cited

U.S. PATENT DOCUMENTS

| | | | |
|---|---|---|---|
| 2,121,463 A | 6/1938 | Wisdom | |
| 5,132,105 A | 7/1992 | Remo | |
| 6,331,209 B1 | 12/2001 | Jang et al. | |
| 6,350,488 B1 | 2/2002 | Lee et al. | |
| 6,514,113 B1 | 2/2003 | Lee et al. | |
| 6,648,711 B1 | 11/2003 | Jang et al. | |
| 6,759,025 B2 | 7/2004 | Hong et al. | |
| 7,118,440 B2 | 10/2006 | Kuo et al. | |
| 7,452,735 B2 | 11/2008 | Li et al. | |
| 7,462,498 B2 | 12/2008 | Mao et al. | |
| 7,611,906 B2 | 11/2009 | Yaniv | |
| 7,619,257 B2 | 11/2009 | Pfeiffer | |
| 7,781,061 B2 | 8/2010 | Garcia et al. | |

| | | |
|---|---|---|
| 8,007,588 B2 | 8/2011 | Ito et al. |
| 8,062,697 B2 | 11/2011 | Yaniv et al. |
| 8,129,463 B2 | 3/2012 | Mao et al. |
| 8,455,047 B2 | 6/2013 | Li et al. |
| 8,668,952 B2 | 3/2014 | Hikata et al. |
| 8,784,663 B2 | 7/2014 | Wei et al. |
| 8,803,636 B2 | 8/2014 | Ermolov |
| 8,865,268 B2 | 10/2014 | Haque et al. |
| 8,952,477 B2 | 2/2015 | Yamada et al. |
| 9,080,928 B2 | 7/2015 | Borini et al. |
| 9,099,252 B2 | 8/2015 | Liu et al. |
| 9,202,639 B2 | 12/2015 | Wei et al. |
| 9,290,389 B2 | 3/2016 | Haque et al. |
| 9,362,565 B2 | 6/2016 | Wei et al. |
| 9,380,979 B2 | 7/2016 | White et al. |
| 9,406,985 B2 | 8/2016 | Amaratunga et al. |
| 9,413,032 B2 | 8/2016 | Wei et al. |
| 9,440,857 B2 | 9/2016 | Sorensen et al. |
| 9,440,858 B2 | 9/2016 | Lipka et al. |
| 9,446,965 B2 | 9/2016 | Kverel et al. |
| 9,490,658 B2 | 11/2016 | Wei et al. |

(Continued)

FOREIGN PATENT DOCUMENTS

| | | |
|---|---|---|
| AU | 2018201650 A1 | 9/2018 |
| AU | 2021361326 A1 | 5/2023 |

(Continued)

OTHER PUBLICATIONS

Chen, Xi'an et al., "Sulfur-doped porous reduced graphene oxide hollow nanospheres framework as metal-free electrocatalysts for oxygen reduction reaction and supercapacitor electrode materials," Nanoscale, Sep. 2014, DOI: 10.1039/C4NR04783D, The Royal Society of Chemistry, pp. 1-7.

You, Chenghang et al., "Uniform nitrogen and sulfur co-doped carbonnanospheres as catalysts for the oxygenreduction reaction," Carbon, vol. 69, Apr. 2014, pp. 294-301.

International Search Report and Written Opinion for PCT Application No. PCT/US2022/072424, dated Sep. 6, 2022, 9 pages.

Hassani, et al., A simple synthesis of sulfur-doped graphene using sulfur powder by chemical vapor deposition, RDC Adv. 2016; 6: 27159-27163 (Year: 2016).

International Preliminary Report On Patentability for PCT Application No. PCT/US2023/063428, dated Sep. 19, 2024, 6 pages.

International Preliminary Report On Patentability for PCT Application No. PCT/US2023/063430, dated Sep. 19, 2024, 8 pages.

International Preliminary Report On Patentability for PCT Application No. PCT/US2023/063431, dated Sep. 19, 2024, 8 pages.

(Continued)

*Primary Examiner* — Shirley V Gembeh

(74) *Attorney, Agent, or Firm* — Abel Schillinger, LLP

(57) ABSTRACT

The present disclosure relates to a cancer treatment delivery method that may include preparing a cancer treatment delivery component that may include a carbon-based nanomaterial composition and a cancer treatment composition attached to the carbon-based nanomaterial composition, delivering the cancer treatment delivery component to a treatment location, and applying a radio frequency to the cancer treatment delivery component at the treatment location. The radio frequency may be configured to heat the cancer treatment delivery component and cause the cancer treatment composition to detach from the carbon-based nanomaterial composition for delivery at the treatment location.

20 Claims, 4 Drawing Sheets

(56) References Cited

U.S. PATENT DOCUMENTS

| | | | |
|---|---|---|---|
| 9,496,435 | B2 | 11/2016 | Wang et al. |
| 9,601,763 | B2 | 3/2017 | Fang et al. |
| 9,660,003 | B2 | 5/2017 | Sato et al. |
| 9,670,066 | B2 | 6/2017 | Lipka et al. |
| 9,676,621 | B2 | 6/2017 | Chen et al. |
| 9,761,380 | B2 | 9/2017 | Wei et al. |
| 9,765,271 | B2 | 9/2017 | Myrick |
| 9,767,992 | B1 | 9/2017 | Stowell et al. |
| 9,782,739 | B2 | 10/2017 | Laine |
| 9,786,444 | B2 | 10/2017 | Hiralal et al. |
| 9,824,789 | B2 | 11/2017 | Pei et al. |
| 9,859,515 | B2 | 1/2018 | Hammond et al. |
| 9,862,602 | B1 | 1/2018 | Riso et al. |
| 9,862,606 | B1 | 1/2018 | Cook et al. |
| 9,887,352 | B2 | 2/2018 | Bessonov et al. |
| 9,905,373 | B2 | 2/2018 | Zhamu et al. |
| 9,917,299 | B2 | 3/2018 | Behan et al. |
| 9,923,206 | B2 | 3/2018 | Chen et al. |
| 9,925,559 | B2 | 3/2018 | Lee et al. |
| 9,945,765 | B2 | 4/2018 | White et al. |
| 9,978,940 | B2 | 5/2018 | Bessonov et al. |
| 9,997,334 | B1 | 6/2018 | Anzelmo et al. |
| 9,997,784 | B2 | 6/2018 | Su et al. |
| 10,069,139 | B2 | 9/2018 | Wang et al. |
| 10,294,133 | B2 | 5/2019 | Hashim et al. |
| 10,316,215 | B2 | 6/2019 | Castaño Meneses |
| 10,326,135 | B2 | 6/2019 | Fasching et al. |
| 10,364,401 | B2 | 7/2019 | Soto-Castillo et al. |
| 10,401,701 | B2 | 9/2019 | Coklin et al. |
| 10,416,519 | B2 | 9/2019 | Conklin et al. |
| 10,428,197 | B2 | 10/2019 | Anzelmo et al. |
| 10,465,128 | B2 | 11/2019 | Cruz et al. |
| 10,472,497 | B2 | 11/2019 | Stowell et al. |
| 10,502,705 | B2 | 12/2019 | Stowell et al. |
| 10,611,979 | B2 | 4/2020 | Diloyan et al. |
| 10,637,043 | B2 | 4/2020 | Zhamu et al. |
| 10,665,724 | B2 | 5/2020 | Pohjonen et al. |
| 10,690,047 | B1 | 6/2020 | LaStella |
| 10,734,653 | B2 | 8/2020 | Lanning et al. |
| 10,756,334 | B2 | 8/2020 | Stowell et al. |
| 10,781,103 | B2 | 9/2020 | Tanner et al. |
| 10,819,313 | B2 | 10/2020 | Voutilainen |
| 10,822,542 | B2 | 11/2020 | Zhong et al. |
| 10,847,704 | B2 | 11/2020 | Sugiura et al. |
| 10,858,755 | B2 | 12/2020 | Kula et al. |
| 10,920,035 | B2 | 2/2021 | Rogojina et al. |
| 10,943,076 | B2 | 3/2021 | Stowell et al. |
| 10,982,119 | B2 | 4/2021 | El-Kady et al. |
| 11,045,427 | B2 | 6/2021 | John et al. |
| 11,107,662 | B2 | 8/2021 | Stowell et al. |
| 11,120,977 | B2 | 9/2021 | Fabien et al. |
| 11,127,941 | B2 | 9/2021 | Lanning et al. |
| 11,127,942 | B2 | 9/2021 | Gazda et al. |
| 11,133,495 | B2 | 9/2021 | Gazda et al. |
| 11,137,368 | B2 | 10/2021 | Stowell et al. |
| 11,198,611 | B2 | 12/2021 | Lanning et al. |
| 11,222,756 | B2 | 1/2022 | Tang et al. |
| 11,224,859 | B2 | 1/2022 | Rong et al. |
| 11,309,545 | B2 | 4/2022 | Kumar et al. |
| 11,335,911 | B2 | 5/2022 | Lanning et al. |
| 11,342,561 | B2 | 5/2022 | Rogojina et al. |
| 11,352,481 | B2 | 6/2022 | Stowell et al. |
| 11,367,895 | B1 | 6/2022 | Shan et al. |
| 11,398,622 | B2 | 7/2022 | Gazda et al. |
| 11,404,692 | B1 | 8/2022 | Lanning et al. |
| 11,433,369 | B1 | 9/2022 | Nicole et al. |
| 11,446,966 | B2 | 9/2022 | Stowell et al. |
| 11,479,062 | B2 | 10/2022 | Stowell et al. |
| 11,489,161 | B2 | 11/2022 | Kumar et al. |
| 11,508,966 | B2 | 11/2022 | Bell et al. |
| 11,511,997 | B2 | 11/2022 | Lim et al. |
| 11,539,074 | B2 | 12/2022 | Rogojina et al. |
| 11,553,630 | B2 | 1/2023 | Kaner et al. |
| 11,555,748 | B2 | 1/2023 | Stowell et al. |
| 11,555,761 | B1 | 1/2023 | Stowell |
| 11,555,799 | B2 | 1/2023 | Lanning et al. |
| 11,585,731 | B2 | 2/2023 | Stowell et al. |
| 11,591,457 | B1 | 2/2023 | Khan et al. |
| 11,592,279 | B2 | 2/2023 | Stowell et al. |
| 11,600,876 | B2 | 3/2023 | Gazda |
| 11,613,817 | B2 | 3/2023 | Stowell et al. |
| 11,623,197 | B2 | 4/2023 | Stowell et al. |
| 11,631,893 | B2 | 4/2023 | Rogojina et al. |
| 11,656,070 | B2 | 5/2023 | Stowell et al. |
| 11,670,826 | B2 | 6/2023 | Gazda |
| 11,674,031 | B1 | 6/2023 | Anzelmo et al. |
| 11,680,012 | B2 | 6/2023 | Stowell et al. |
| 11,688,895 | B1 | 6/2023 | Gibbs et al. |
| 11,719,582 | B2 | 8/2023 | Stowell et al. |
| 11,735,745 | B2 | 8/2023 | Vanheusden et al. |
| 11,739,409 | B2 | 8/2023 | Stowell et al. |
| 11,761,057 | B1 | 9/2023 | Stowell et al. |
| 11,796,883 | B2 | 10/2023 | Conklin et al. |
| 11,814,292 | B2 | 11/2023 | El-Kady et al. |
| 11,897,768 | B2 | 2/2024 | Ashton et al. |
| 12,371,326 | B2 | 7/2025 | Johnson et al. |
| 2006/0062715 | A1 | 3/2006 | Endo et al. |
| 2006/0078730 | A1 | 4/2006 | Tsukada et al. |
| 2006/0093545 | A1 | 5/2006 | Maruyama et al. |
| 2006/0196763 | A1 | 9/2006 | Choi et al. |
| 2006/0216517 | A1 | 9/2006 | Handa et al. |
| 2006/0217025 | A1 | 9/2006 | Hsiao et al. |
| 2006/0263588 | A1 | 11/2006 | Handa et al. |
| 2008/0241047 | A1 | 10/2008 | Asano |
| 2008/0254296 | A1 | 10/2008 | Handa et al. |
| 2009/0035570 | A1 | 2/2009 | Mao et al. |
| 2009/0047428 | A1 | 2/2009 | Shan et al. |
| 2009/0121606 | A1 | 5/2009 | Okubo et al. |
| 2009/0124746 | A1 | 5/2009 | Handa et al. |
| 2009/0131575 | A1 | 5/2009 | Handa et al. |
| 2009/0135042 | A1 | 5/2009 | Umishita et al. |
| 2009/0152508 | A1 | 6/2009 | Handa et al. |
| 2009/0162636 | A1 | 6/2009 | Shan et al. |
| 2009/0226712 | A1 | 9/2009 | Handa et al. |
| 2009/0247796 | A1 | 10/2009 | Waycuilis et al. |
| 2009/0261186 | A1 | 10/2009 | Fink et al. |
| 2009/0263642 | A1 | 10/2009 | Handa et al. |
| 2009/0292057 | A1 | 11/2009 | Handa et al. |
| 2010/0149018 | A1 | 6/2010 | Umishita et al. |
| 2010/0181534 | A1 | 7/2010 | Shenderova et al. |
| 2010/0310447 | A1 | 12/2010 | Yaniv et al. |
| 2011/0027603 | A1 | 2/2011 | Yaniv et al. |
| 2011/0045273 | A1 | 2/2011 | Handa et al. |
| 2011/0147647 | A1 | 6/2011 | Yaniv et al. |
| 2011/0175065 | A1 | 7/2011 | de la Vega et al. |
| 2012/0082787 | A1 | 4/2012 | Fujita |
| 2012/0315482 | A1 | 12/2012 | Muramatsu et al. |
| 2013/0316092 | A1 | 11/2013 | Chen et al. |
| 2014/0216942 | A1 | 8/2014 | Jiang et al. |
| 2014/0235513 | A1 | 8/2014 | Kverel et al. |
| 2014/0335010 | A1 | 11/2014 | Sorensen et al. |
| 2015/0004667 | A1 | 1/2015 | McKinney et al. |
| 2015/0017699 | A1 | 1/2015 | McKinney et al. |
| 2015/0047687 | A1 | 2/2015 | Conklin et al. |
| 2015/0047697 | A1 | 2/2015 | Conklin et al. |
| 2015/0047882 | A1 | 2/2015 | Jiang et al. |
| 2015/0060817 | A1 | 3/2015 | Sato et al. |
| 2015/0155127 | A1 | 6/2015 | Fink et al. |
| 2016/0130149 | A1 | 5/2016 | Shankman |
| 2016/0225991 | A1 | 8/2016 | Schwab et al. |
| 2016/0240861 | A1 | 8/2016 | Kurungot et al. |
| 2016/0329586 | A1 | 11/2016 | Ninan et al. |
| 2017/0179314 | A1 | 6/2017 | Novoselov et al. |
| 2017/0278643 | A1 | 9/2017 | El-Kady et al. |
| 2018/0207591 | A1 | 7/2018 | Yu et al. |
| 2018/0248175 | A1 | 8/2018 | Ghezelbash et al. |
| 2018/0261847 | A1 | 9/2018 | Su et al. |
| 2018/0265359 | A1 | 9/2018 | Cross |
| 2018/0305570 | A1 | 10/2018 | El-Kady et al. |
| 2018/0320586 | A1 | 11/2018 | Johnson et al. |
| 2018/0346337 | A1 | 12/2018 | Tour et al. |
| 2018/0366280 | A1 | 12/2018 | Hwang et al. |
| 2018/0370801 | A1 | 12/2018 | Patole |
| 2019/0031906 | A1 | 1/2019 | Kim et al. |

(56)  References Cited

U.S. PATENT DOCUMENTS

| | | |
|---|---|---|
| 2019/0039907 A1 | 2/2019 | Zeng et al. |
| 2019/0048161 A1 | 2/2019 | Zeng et al. |
| 2019/0088420 A1 | 3/2019 | Tour et al. |
| 2019/0100658 A1 | 4/2019 | Taylor et al. |
| 2019/0109317 A1 | 4/2019 | Zhou et al. |
| 2019/0161352 A1 | 5/2019 | Price |
| 2020/0040444 A1 | 2/2020 | Stowell et al. |
| 2020/0066474 A1 | 2/2020 | Lorr et al. |
| 2020/0112026 A1 | 4/2020 | Tour et al. |
| 2020/0173045 A1 | 6/2020 | Chen et al. |
| 2020/0243846 A1 | 7/2020 | He et al. |
| 2020/0246179 A1 | 8/2020 | Peyman |
| 2020/0274181 A1 | 8/2020 | Park et al. |
| 2020/0294779 A1 | 9/2020 | Ashton et al. |
| 2020/0294780 A1 | 9/2020 | Ashton et al. |
| 2020/0298174 A1 | 9/2020 | Boudreault |
| 2020/0302328 A1 | 9/2020 | Nafradi et al. |
| 2020/0369526 A1 | 11/2020 | Ladislaus et al. |
| 2020/0402768 A1 | 12/2020 | Stowell et al. |
| 2021/0017031 A1 | 1/2021 | Hardman et al. |
| 2021/0053829 A1 | 2/2021 | Tanner et al. |
| 2021/0114886 A1 | 4/2021 | Rohani et al. |
| 2021/0172904 A1 | 6/2021 | Stowell et al. |
| 2021/0172905 A1 | 6/2021 | Stowell et al. |
| 2021/0181145 A1 | 6/2021 | Stowell et al. |
| 2021/0181146 A1 | 6/2021 | Stowell et al. |
| 2021/0210753 A1 | 7/2021 | Gazda et al. |
| 2021/0218110 A1 | 7/2021 | Lanning et al. |
| 2021/0226225 A1 | 7/2021 | Lanning et al. |
| 2021/0226302 A1 | 7/2021 | Lanning et al. |
| 2021/0238040 A1 | 8/2021 | Opoku et al. |
| 2021/0242505 A1 | 8/2021 | Gazda et al. |
| 2021/0257666 A1 | 8/2021 | Huang et al. |
| 2021/0257667 A1 | 8/2021 | Gazda et al. |
| 2021/0359306 A1 | 11/2021 | Rogojina et al. |
| 2021/0359308 A1 | 11/2021 | Huang et al. |
| 2021/0396708 A1 | 12/2021 | Lim et al. |
| 2021/0396709 A1 | 12/2021 | Lim et al. |
| 2021/0401685 A1 | 12/2021 | Martínez Rovira et al. |
| 2022/0030874 A1 | 2/2022 | Castaño Meneses et al. |
| 2022/0091066 A1 | 3/2022 | Lim et al. |
| 2022/0185676 A1 | 6/2022 | Mahiko et al. |
| 2022/0263111 A1 | 8/2022 | Li et al. |
| 2022/0271291 A1 | 8/2022 | Li et al. |
| 2022/0274062 A1 | 9/2022 | Moxon et al. |
| 2022/0320515 A1 | 10/2022 | Rogojina et al. |
| 2022/0380218 A1 | 12/2022 | Johnson et al. |
| 2022/0407046 A1 | 12/2022 | Gazda et al. |
| 2023/0017082 A1 | 1/2023 | Stowell et al. |
| 2023/0019088 A1 | 1/2023 | Montalvo et al. |
| 2023/0021737 A1 | 1/2023 | Stowell et al. |
| 2023/0031884 A1 | 2/2023 | Bugga et al. |
| 2023/0035035 A1 | 2/2023 | Rogojina et al. |
| 2023/0035506 A1 | 2/2023 | Rogojina et al. |
| 2023/0040722 A1 | 2/2023 | Stowell et al. |
| 2023/0069456 A1 | 3/2023 | Stowell et al. |
| 2023/0074143 A1 | 3/2023 | Stowell et al. |
| 2023/0109645 A1 | 4/2023 | Stowell et al. |
| 2023/0145800 A1 | 5/2023 | Stowell et al. |
| 2023/0147825 A1 | 5/2023 | Stowell et al. |
| 2023/0187744 A1 | 6/2023 | Gazda |
| 2023/0192491 A1 | 6/2023 | Johnson et al. |
| 2023/0192493 A1 | 6/2023 | Johnson et al. |
| 2023/0192495 A1 | 6/2023 | Johnson et al. |
| 2023/0193040 A1 | 6/2023 | Johnson et al. |
| 2023/0193041 A1 | 6/2023 | Johnson et al. |
| 2023/0212729 A1 | 7/2023 | Stowell et al. |
| 2023/0275257 A1 | 8/2023 | Bell et al. |
| 2023/0278863 A1 | 9/2023 | Johnson et al. |
| 2023/0278864 A1 | 9/2023 | Johnson et al. |
| 2023/0278865 A1 | 9/2023 | Johnson et al. |
| 2023/0278866 A1 | 9/2023 | Johnson et al. |
| 2023/0278867 A1 | 9/2023 | Johnson et al. |
| 2023/0278869 A1 | 9/2023 | Johnson et al. |
| 2023/0278870 A1 | 9/2023 | Johnson et al. |
| 2023/0278871 A1 | 9/2023 | Johnson et al. |
| 2023/0278872 A1 | 9/2023 | Johnson et al. |
| 2023/0278873 A1 | 9/2023 | Johnson et al. |
| 2023/0287197 A1 | 9/2023 | Anzelmo et al. |
| 2023/0296479 A1 | 9/2023 | Stowell et al. |
| 2023/0373866 A1 | 11/2023 | Johnson et al. |
| 2023/0373867 A1 | 11/2023 | Johnson et al. |
| 2023/0382736 A1 | 11/2023 | Johnson et al. |
| 2023/0392541 A1 | 12/2023 | Johnson et al. |
| 2023/0399564 A1 | 12/2023 | Edler et al. |
| 2024/0052954 A1 | 2/2024 | Banerji et al. |
| 2024/0180960 A1 | 6/2024 | Petrello et al. |
| 2024/0181061 A1 | 6/2024 | Johnson et al. |

FOREIGN PATENT DOCUMENTS

| | | | |
|---|---|---|---|
| BY | 10010 C1 | 12/2007 | |
| BY | 21633 C1 | 2/2018 | |
| CN | 105600780 A | 5/2016 | |
| CN | 105836729 A | 8/2016 | |
| CN | 106328909 A | 1/2017 | |
| CN | 106532026 A | 3/2017 | |
| CN | 107416819 A | 12/2017 | |
| CN | 107579203 A | 1/2018 | |
| CN | 108199058 A | 6/2018 | |
| CN | 108352493 A | 7/2018 | |
| CN | 108658061 A | 10/2018 | |
| CN | 108946710 A | 12/2018 | |
| CN | 109516452 A | 3/2019 | |
| CN | 110327372 * | 10/2019 | ............ C01B 32/15 |
| CN | 110451514 A | 11/2019 | |
| CN | 110734077 A | 1/2020 | |
| CN | 110787827 A | 2/2020 | |
| CN | 108383102 B | 4/2020 | |
| CN | 108946710 B | 4/2020 | |
| CN | 111186830 A | 5/2020 | |
| CN | 111196602 A | 5/2020 | |
| CN | 111467499 A | 7/2020 | |
| CN | 112079349 A | 12/2020 | |
| CN | 109200059 B | 3/2021 | |
| CN | 112645312 A | 4/2021 | |
| CN | 116043186 A | 5/2023 | |
| CN | 116075361 A | 5/2023 | |
| CN | 116234942 A | 6/2023 | |
| EA | 11588 B1 | 4/2009 | |
| EP | 2857550 A1 | 4/2015 | |
| EP | 3213349 B1 | 6/2019 | |
| EP | 2489088 B1 | 7/2019 | |
| EP | 3950586 A1 | 2/2022 | |
| EP | 4230774 A1 | 8/2023 | |
| EP | 3914744 B1 | 12/2023 | |
| GB | 2618142 A | 11/2023 | |
| JP | H0578173 A | 3/1993 | |
| JP | H05070115 A | 3/1993 | |
| JP | 2003335508 A | 11/2003 | |
| JP | 2004526652 A | 9/2004 | |
| JP | 2007091495 A | 4/2007 | |
| JP | 2009274952 A | 11/2009 | |
| JP | 2010052972 A | 3/2010 | |
| JP | 5578640 B2 | 8/2014 | |
| JP | 2015050245 A | 3/2015 | |
| JP | 2015189606 A | 11/2015 | |
| JP | 6097908 B2 | 3/2017 | |
| JP | 2017045639 A | 3/2017 | |
| JP | 2017197424 A | 11/2017 | |
| JP | 2018504341 A | 2/2018 | |
| JP | 2018037617 A | 3/2018 | |
| JP | 2018048368 A | 3/2018 | |
| JP | 6455942 B2 | 1/2019 | |
| JP | 2020506153 A | 2/2020 | |
| JP | 6754355 B2 | 9/2020 | |
| JP | 2021120331 A | 8/2021 | |
| JP | 6934149 B2 | 9/2021 | |
| JP | 7041421 B2 | 3/2022 | |
| KR | 1020110030570 A | 3/2011 | |
| KR | 101451140 B1 | 10/2014 | |
| KR | 20150121680 A | 10/2015 | |
| KR | 1020150124636 A | 11/2015 | |
| KR | 1020160050926 A | 5/2016 | |

(56) References Cited

FOREIGN PATENT DOCUMENTS

| | | | |
|------|------------------|-----|---------|
| KR | 20170044836 | A | 4/2017 |
| KR | 1020200039715 | A | 4/2020 |
| KR | 20210088074 | A | 7/2021 |
| KR | 20210105107 | A | 8/2021 |
| KR | 20210113319 | A | 9/2021 |
| KR | 1020210144756 | A | 11/2021 |
| RU | 2393276 | C1 | 6/2010 |
| RU | 2591942 | C2 | 7/2016 |
| RU | 2641829 | C1 | 1/2018 |
| RU | 2658036 | C1 | 6/2018 |
| TW | 201834965 | A | 10/2018 |
| TW | 202104076 | A | 2/2021 |
| TW | 202218224 | A | 5/2022 |
| WO | 2010003922 | A1 | 1/2010 |
| WO | 2010049637 | A1 | 5/2010 |
| WO | 2010110153 | A1 | 9/2010 |
| WO | 2014011402 | A1 | 1/2014 |
| WO | 2014052376 | A1 | 4/2014 |
| WO | 2014077507 | A1 | 5/2014 |
| WO | 2015009758 | A1 | 1/2015 |
| WO | 2015025147 | A1 | 2/2015 |
| WO | 2015049624 | A1 | 4/2015 |
| WO | 2015059718 | A1 | 4/2015 |
| WO | 2016002277 | A1 | 1/2016 |
| WO | 2016011223 | A1 | 1/2016 |
| WO | 2016175195 | A1 | 11/2016 |
| WO | 2017009040 | A1 | 1/2017 |
| WO | 2018148044 | A2 | 8/2018 |
| WO | WO 2018/148044 | * | 8/2018 ........ H01J 37/32532 |
| WO | 2019014212 | A1 | 1/2019 |
| WO | 2019126782 | A1 | 6/2019 |
| WO | 2020092449 | A1 | 5/2020 |
| WO | 2020257229 | A2 | 12/2020 |
| WO | 2021080664 | A1 | 4/2021 |
| WO | 2021158395 | A1 | 8/2021 |
| WO | 2021168444 | A1 | 8/2021 |
| WO | 2021183931 | A1 | 9/2021 |
| WO | 2021237282 | A1 | 12/2021 |
| WO | 2022080142 | A1 | 4/2022 |
| WO | 2022086611 | A1 | 4/2022 |
| WO | 2022212114 | A1 | 10/2022 |
| WO | 2022216403 | A1 | 10/2022 |
| WO | 2022223668 | A1 | 10/2022 |
| WO | 2022246443 | A1 | 11/2022 |
| WO | 2022266393 | A1 | 12/2022 |
| WO | 2023003893 | A1 | 1/2023 |
| WO | 2023004060 | A2 | 1/2023 |
| WO | 2023023187 | A1 | 2/2023 |
| WO | 2023039204 | A1 | 3/2023 |
| WO | 2023090990 | A1 | 5/2023 |
| WO | 2023122652 | A1 | 6/2023 |
| WO | 2023122658 | A1 | 6/2023 |
| WO | 2023122660 | A1 | 6/2023 |
| WO | 2023122664 | A1 | 6/2023 |
| WO | 2023122668 | A1 | 6/2023 |
| WO | 2023168219 | A1 | 9/2023 |
| WO | 2023168220 | A1 | 9/2023 |
| WO | 2023168221 | A1 | 9/2023 |
| WO | 2023168223 | A1 | 9/2023 |
| WO | 2023168224 | A1 | 9/2023 |
| WO | 2023168225 | A1 | 9/2023 |
| WO | 2023168228 | A1 | 9/2023 |
| WO | 2023168229 | A1 | 9/2023 |
| WO | 2023168230 | A1 | 9/2023 |
| WO | 2023168231 | A1 | 9/2023 |
| WO | 2023168263 | A1 | 9/2023 |
| WO | 2023173027 | A1 | 9/2023 |
| WO | 2023173045 | A1 | 9/2023 |
| WO | 2023225285 | A1 | 11/2023 |
| WO | 2023225290 | A1 | 11/2023 |
| WO | 2023229933 | A1 | 11/2023 |
| WO | 2024123779 | A1 | 6/2024 |
| WO | 2024123782 | A1 | 6/2024 |
| WO | 2024123787 | A1 | 6/2024 |

OTHER PUBLICATIONS

Nepal, et al., One-step synthesisof graphene via catalyst-free gas-phase hydrocarbon detonation, Nanotechnology 2013; 24: 245602, pp. 1-7, with Supporting Information. (Year 2013).

International Search Report and Written Opinion for PCT Application No. PCT/US2022/082122, dated Apr. 19, 2023, 11 pages.

International Search Report and Written Opinion for PCT Application No. PCT/US2022/082130, dated Apr. 20, 2023, 13 pages.

International Search Report and Written Opinion for PCT Application No. PCT/US2022/082134, dated Apr. 19, 2023, 11 pages.

International Search Report and Written Opinion for PCT Application No. PCT/US2022/082138, dated May 1, 2023, 11 pages .

Nitze, Florian et al., "Sulfur-doped ordered mesoporous carbons: A stability-improving sulfur host for lithium-sulfer battery cathodes," Journal of Power Sources, 317, dated 2016, pp. 112-119.

International Search Report and Written Opinion for PCT Application No. PCT/US2022/082142, dated May 1, 2023, 12 pages.

Hasan, Maria et al., "Direct Chemical Vapor Deposition Synthesis of Large Area Single-Layer Brominated Graphene", The Royal Society of Chemistry, RSC Advances, May 1, 2019, pp. 13527-13532, vol. 9.

Xiaorong, Zou et al., "A Method for Selective Bromination of Graphene and its Use for Subsequent Functionalization with Aromatic Molecules", Materials Research Express, Feb. 28, 2017, pp. 1-8, vol. 4, IOP Science.

Lisichkin, G. V.et al., "Halogenation of Detonation-Synthesised Nanodiamond Surfaces", Mendeleev Communications, Jan. 27, 2009, pp. 309-310, vol. 19, No. 6. ScienceDirect.

Zhan, Y. et al., "Iodine Doped Graphene as Anode Material for Lithium Ion Battery", Carbon, Mar. 13, 2015, pp. 1-8, vol. 94.

Chen, Z. et al., "Oxygen-Doped Hierarchical Porous Carbon with Improved Selectivity of Hydrogen Peroxide in an Oxygen Reduction Reaction", Energy & Fuels, May 15, 2021, pp. 2665-2673, vol. 35.

Tavakol, H. et al. "Synthesis of Multi-Walled Phosphorus and Sulfur Co-Doped CNTs" Fullerenes, Nanotubes and Carbon Nanostructures, Oct. 22, 2018, pp. 715-721, vol. 26, No. 11.

Pappas, G. S. et al., "Heteroatom Doped-Carbon Nanospheres as Anodes in Lithium Ion Batteries", Materials, Jan. 9, 2016, pp. 1-13, vol. 9. MDPI, Basel Switzerland.

Wang, X. et al., "Heteroatom-Doped Graphene Materials: Syntheses, Properties and Applications", Chemical Society Reviews, Jun. 23, 2014, pp. 7067-7098, vol. 43.

Kaushal, S. et al., "Heteroatom-Doped Graphene as Sensing Materials: A Mini Review", RSC Advances, Aug. 4, 2020, pp. 28608-28629, vol. 10.

Lubwama, M. et al. "Characteristics and Tribological Performance of DLC and Si-DLC Films Deposited on Nitrile Rubber", Surface and Coatings Technology, May 12, 2012, pp. 4584-4593, vol. 206.

Qian, Z. et al., "Si-Doped Carbon Quantum Dots: a Facile and General Preparation Strategy, Bioimaging Application, and Multifunctional Sensor", ACS Applied Materials & Interfaces, April, 8, 2014, pp. 6797-6805, vol. 6, No. 9.

Tachikawa, H. et al., "Hydrogen Storage Mechanism in Sodium-Based Graphene Nanoflakes: A Density Functional Theory Study", Hydrogen, Jan. 19, 2022, pp. 43-52, vol. 3, No. 1. MDPI, Basel, Switzerland.

Markus, B. G. et al., "Ultralong Spin Lifetime in Light Alkali Atom Doped Graphene", ACS Nano, Jun. 2, 2020, pp. 7492-7501, No. 14. ACS Publications.

International Search Report and Written Opinion for PCT Application No. PCT/US2023/063417, dated Jun. 9, 2023, 11 pages.

International Search Report and Written Opinion for PCT Application No. PCT/US2023/063419, dated Jun. 20, 2023, 10 pages.

International Search Report and Written Opinion for PCT Application No. PCT/US2023/063420, dated Jun. 8, 2023, 11 pages.

International Search Report and Written Opinion for PCT Application No. PCT/US2023/063422, dated Jun. 15, 2023, 11 pages.

International Search Report and Written Opinion for PCT Application No. PCT/US2023/063423, dated Jun. 15, 2023, 11 pages.

(56)　　　　References Cited

OTHER PUBLICATIONS

International Search Report and Written Opinion for PCT Application No. PCT/US2023/063424, dated Jun. 15, 2023, 11 pages.
International Search Report and Written Opinion for PCT Application No. PCT/US2023/063427, dated Jun. 20, 2023, 10 pages.
International Search Report and Written Opinion for PCT Application No. PCT/US2023/063428, dated Jun. 20, 2023, 9 pages.
International Search Report and Written Opinion for PCT Application No. PCT/US2023/063430, dated Jun. 15, 2023, 11 pages.
International Search Report and Written Opinion for PCT Application No. PCT/US2023/063431, dated Jun. 15, 2023, 11 pages.
International Search Report and Written Opinion for PCT Application No. PCT/US2023/022885, dated Sep. 12, 2023, 11 pages.
International Search Report and Written Opinion for PCT Application No. PCT/US2023/022892, dated Sep. 7, 2023, 11 pages.
International Search Report and Written Opinion for PCT Application No. PCT/US2023/022899, dated Sep. 5, 2023, 11 pages.
International Search Report and Written Opinion for PCT Application No. PCT/US2023/082529, dated Apr. 9, 2024, 13 pages.
International Search Report and Written Opinion for PCT Application No. PCT/US2023/082535, dated Apr. 24, 2024, 11 pages.
International Search Report and Written Opinion for PCT Application No. PCT/US2023/082541, dated Apr. 12, 2024, 12 pages.
Tang et al. "Versatile carbon nanoplatforms for cancer treatment and diagnosis: strategies, applications and future perspectives.", Theranostics, 2022(Epub. Feb. 21, 2022), vol. 12, issue 5, pp. 2290-2321.
Rejinold et al, "Radio frequency responsive nano-biomaterials for cancer therapy", Journal of Controlled Release, 2015, vol. 204, pp. 85-97.
Pumprla et al., "Non-contact radiofrequency-induced reduction of subcutaneous abdominal fat correlates with initial cardiovascular autonomic balance and fat tissue hormones: safety analysis." F1000Res. Feb. 20, 2015; Version 1, 4:49. doi: 10.12688/f1000research.5708.1. PMID: 26069728; PMCID: PMC4431383, pp. 1-20, <https://www.ncbi.nlm.nih.gov/pmc/articles/PMC4431383/>.
International Preliminary Report On Patentability for PCT Application No. PCT/US2022/072424, dated Nov. 30, 2023, 7 pages.
International Preliminary Report On Patentability for PCT Application No. PCT/US2022/082122, dated Jul. 4, 2024, 8 pages.
International Preliminary Report On Patentability for PCT Application No. PCT/US2022/082130, dated Jul. 4, 2024, 9 pages.
International Preliminary Report On Patentability for PCT Application No. PCT/US2022/082134, dated Jul. 4, 2024, 8 pages.
International Preliminary Report On Patentability for PCT Application No. PCT/US2022/082138, dated Jul. 4, 2024, 8 pages.
International Preliminary Report On Patentability for PCT Application No. PCT/US2022/082142, dated Jul. 4, 2024, 8 pages.
Teng et al., "Fabrication and Characterization of Nanocarbon-Based Nanofluids by Using an Oxygen-Acetylene Flame Synthesis System," in Nanoscale Research Letters, 11:288 (2016), pp. 1-13 (Year: 2016).
Choma et al., "Development of Mesoporosity in Carbon Spheres Obtained by Stober Method", Microporous and Mesoporous Materials 185 (2014), 197-203. (Year: 2014).
Nepal, Arjun et al., "One-step synthesis of graphene via catalyst-free gas-phase hydrocarbon detonation," IOP Science, Nanotechnology, vol. 24, No. 24, published May 20, 2013, 3 pages <https://iopscience.iop.org/ article/10.1088/0957-4484/24/24/245602>.
Galeon, Dom, "We May Finally Have a Way of Mass Producing Graphene," Futurism, dated Jan. 28, 2017, 7 pages, <https://futurism.com/we-may-finally-have-a-way-of-mass-producing-graphene>.
"Graphene Mass Produce," Google Search, <https://www.google.com/search?q=graphene*mass*produce&ie=UTF-8&oe=UTF-8&hl=en-us&client=safari>.
<https://firstgraphene.net/>.
<https://www.jmtour.com/media/Flash%20Graphene%20Video%20Rice%20University%202019.mp4>.

Ramirez, Giovanni et al., "Tribochemical Conversion of Methane to Graphene and Other Carbon Nanostructures: Implications for Friction and Wear," ACS Appl. Nano Mater., 2020, 3, 8, 8060-8067, Abstract only.
Wang, Feng et al., "High-purity few-layer graphene from plasma pyrolysis of methane as conductive additive for LiFePO4 lithium ion battery," Journal of Materials Research and Technology, vol. 9, Issue 5, Sep.-Oct. 2020, pp. 10004-10015.
Sorensen, Chris, "Physicists patent detonation technique to mass-produce graphene," Kansas State University, dated Jan. 25, 2017, 4 pages, <https://phys.org/news/2017-01-physicists-patent-detonation-technique-mass-produce.html>.
<https://scx2.b-cdn.net/gfx/news/2017/1-physicistspa.jpg>.
Zhakeyev, Adilet et al., "Additive Manufacturing: Unlocking the Evolution of Energy Materials," Advanced Science, vol. 4, Issue 10, published Jul. 25, 2017, 115 pages.
"Patented process converts petroleum feedstock to graphite, graphene and green hydrogen," First Graphene, ASX Announcement, dated Apr. 20, 2021, 2 pages.
Jiao, Yong et al., "High-performance triboelectric nanogenerators based onblade-coating lead halide perovskite film andelectrospinning PVDF/graphene nanofiber," Chemical Engineering Journal, vol. 483, Mar. 1, 2024, 149442, pp. 1-6.
"Focus on additives: Harnessing the power of graphene incoatings and paints", Polymers Paint Colour Journal, Feb. 20, 2024, pp. 1-11.
Kumar, Vijay et al., "Cavitation-corrosion analysis of HVOF-sprayed WC-Co—Cr-graphene nanoplatelets coatings with LST pre-treatment", International Journal of Refractory Metals and Hard Materials, vol. 120, Apr. 2024, 106610, pp. 1-6.
Li, Li et al., "Hydrophobic and anti-fouling novel anti-corrosion coatings of graphene quantum dots in situ doped withpolyphenylene sulfide", Surface and Coatings Technology, vol. 479, Mar. 15, 2024, 130527, pp. 1-5.
Lim, Yi Shen et al., "Nucleate boiling enhancement on hybrid graphene-nanoplatelets/carbon nanotubes coatings for light-emittingdiode cooling", Applied Thermal Engineering, vol. 244, May, 1, 2024, 122785, pp. 1-27.
Mourya, Punita et al., "Epoxy coating reinforced with graphene-PANI nanocomposites for enhancement of corrosion-resistanceperformance of mild steel in saline water", Colloids and Surfaces A: Physicochemical and Engineering Aspects, vol. 687, Apr. 20, 2024, 133500, pp. 1-6.
Pandey, Usha et al., "Comparative study of graphene oxide-multifunctionaloxide doping on corrosion resistance of electrodepositednickel coatings in saline environments", International Journal of Hydrogen Energy, vol. 60, Mar. 22, 2024, pp. 165-179.
Pang, Wuting et al., "Graphene oxides enhanced polyurethane based compositecoating with long term corrosion resistance and self-healing property", European Polymer Journal, vol. 207, Mar. 6, 2024, 112825, pp. 1-5.
Sama, Deepam. "What is Graphene Coating?Here's everything you must know", pp. 1-13. <https://www.carzspa.com/what-is-graphene-coating/>.
Selim, Mohamed S. et al., "Hierarchical biocide-free silicone/graphene-silicon carbidenanocomposite coatings for marine anti-fouling andsuperhydrophobicity of ship hulls", Chemical Engineering Science, vol. 291, Jun. 5, 2024, 119929, pp. 1-7.
Sy, Kim et al. "In-situ microscopy-assisted meniscus-guided coating forhighly sensitive reduced graphene oxide-basednanocomposite biosensor", Europe PMC Plus, Feb. 22, 2024, pp. 1-2.
GMG Provides Commercialisation Update on Energy SavingsCoating Thermal-XR® (/blogpost/1501180/497649/GMG-Provides-Commercialisation-Update-on-Energy-Savings-Coating-Thermal-XR), Feb. 2, 2024, pp. 1-6. <https://www.thegraphenecouncil.org/blogpost/1501180/497649/GMG-Provides-Commercialisation-Update-on-Energy-Savings-Coating-THERMAL-XR>.
Xie, Chan et al. "Long-lasting anti-corrosion of superhydrophobic coating bysynergistic modification of graphene oxide withpolydopamine and cerium oxide", Construction and Building Materials, vol. 418, Mar. 8, 2024, 135283, pp. 1-5.

(56) References Cited

OTHER PUBLICATIONS

Cao, M.J. et al. "Research progress on graphene production by methane cracking: approach and growth mechanism", Materials Today Sustainability, vol. 24, Aug. 30, 2023, pp. 1-20.

International Preliminary Report On Patentability for PCT Application No. PCT/US2023/063417, dated Sep. 19, 2024, 8 pages.

International Preliminary Report On Patentability for PCT Application No. PCT/US2023/063419, dated Sep. 19, 2024, 7 pages.

International Preliminary Report On Patentability for PCT Application No. PCT/US2023/063420, dated Sep. 19, 2024, 8 pages.

International Preliminary Report On Patentability for PCT Application No. PCT/US2023/063422, dated Sep. 19, 2024, 8 pages.

International Preliminary Report On Patentability for PCT Application No. PCT/US2023/063423, dated Sep. 19, 2024, 8 pages.

International Preliminary Report On Patentability for PCT Application No. PCT/US2023/063424, dated Sep. 19, 2024, 8 pages.

International Preliminary Report On Patentability for PCT Application No. PCT/US2023/063427, dated Sep. 19, 2024, 7 pages.

International Preliminary Report On Patentability for PCT Application No. PCT/US2023/022885, dated Dec. 5, 2024, 8 pages.

International Preliminary Report On Patentability for PCT Application No. PCT/US2023/022892, dated Dec. 5, 2024, 8 pages.

International Preliminary Report On Patentability for PCT Application No. PCT/US2023/022899, dated Dec. 5, 2024, 8 pages.

Cao, M.J. et al., "Research progress on graphene production by methane cracking: approach and growth mechanism", Materials Today Sustainability, vol. 24, Dec. 2023.

International Preliminary Report On Patentability for PCT Application No. PCT/US2023/082529, dated Jun. 19, 2025, 9 pages.

International Preliminary Report On Patentability for PCT Application No. PCT/US2023/082535, dated Jun. 19, 2025, 8 pages.

International Preliminary Report On Patentability for PCT Application No. PCT/US2023/082541, dated Jun. 19, 2025, 8 pages.

Extended European Search Report for EP Application No. 23764053.7, dated Mar. 18, 2026, 10 pages.

Liu, Ziwu et al., "Preparation of Phosphorus-Doped Carbon Nanospheres and Their Electrocatalytic Performance for O2 Reduction," Journal of Natural Gas Chemistry, vol. 21, No. 3, May 1, 2012, pp. 257-264.

Wu, Jiao et al., "Synthesis of Phosphorus-Doped Carbon Hollow Spheres as Efficient Metal-Free Electrocatalysts for Oxygen Reduction," Carbon, Elsevier Oxford, GB, vol. 82, Nov. 11, 2014, pp. 562-571.

Tavakol, Hossein et al., "Synthesis of Multi-Walled Phosphorus and Sulfur Co-Doped CNTs," Fullerenes, Nanotubes and Carbon Nanostructures, vol. 26, No. 11, Oct. 22, 2018, pp. 715-721.

Extended European Search Report for EP Application No. 22912691.7, dated Nov. 7, 2025, 8 pages.

Extended European Search Report for EP Application No. 22912695.8, dated Nov. 18, 2025, 9 pages.

Extended European Search Report for EP Application No. 22912697.4, dated Nov. 25, 2025, 10 pages.

Extended European Search Report for EP Application No. 22912699.0, dated Dec. 1, 2025, 10 pages.

Extended European Search Report for EP Application No. 22912702.2, dated Dec. 10, 2025, 7 pages.

Extended European Search Report for EP Application No. 23764054.5, dated Feb. 2, 2026, 14 pages.

Osswald, S., Yushin, G., Mochalin, V., Kucheyev, S.O., & Gogotsi, Y. (2006), "Control of sp2/sp3 carbon ratio and surface chemistry of nanodiamond powders by selective oxidation in Air," Journal of the American Chemical Society, 128(35), 11635-11642, <https://doi.org/10.1021/ja063303n> (Year: 2006).

Zou et al., "A Composite Consisting of Bromine-Doped Carbon Dots and Ferric Ions as a Fluorescent Probe for Determination and Intracellular Imaging of Phosphate," Microchimica Acta 186, Jul. 2019, 1-9 (Year: 2019).

Zhou et al., "Facile Synthesis of Halogenated Carbon Quantum Dots as an Important Intermediate for Surface Modification," RSC Adv., Apr. 3, 2013, 9625-9628 (Year: 2013).

Knoblauch et al., "Heavy Carbon Nanodots: A New Phosphorescent Carbon Nanostructure," Phys. Chem. Chem. Phys., 20, May 2018, 15518-15527 (Year: 2018).

Huang, C. et al., "Phosphorus, Nitrogen and Oxygen Co-Doped Polymer-Based Core-Shell Carbon Sphere for High-Performance Hybrid Supercapacitors," Electrochimica Acta, vol. 270, dated Apr. 20, 2018, pp. 339-351.

Ye, Zhengqing et al., "Nitrogen and oxygen-codoped carbon nanospheres for excellent specific capacitance and cyclic stability supercapacitor electrodes," Chemical Engineering Journal, vol. 330 (2017) pp. 1166-1173.

Deng, H. et al, "Radial Pores in Nitrogen/Oxygen Dual-Doped Carbon Nanospheres Anode Boost High-Power and Ultrastable Potassium-Ion Batteries," Advanced Functional Materials, vol. 31, Issue 51, (2021), pp. 1-11.

Zhang, Xu et al., "Impact of Chlorine Functionalization on High-Mobility Chemical Vapor Deposition Grown Graphene," ACS Nano, American Chemical Society, vol. 7, No. 8, dated 2013, pp. 7262-7270.

Spicer, P.T. et al., "Flame Synthesis of Composite Carbon Black-Fumed Silica Nanostructured Particles", Journal of Aerosol Science, Elmsford, NY, US, vol. 29, No. 5/06, Jun. 1, 1998, pp. 647-659.

Vital, Andri et al., "One-Step Flame Synthesis of Ultrafine SiO2—C Nanocomposite Particles with High Carbon Loading and Their Carbothermal Conversion," Industrial & Engineering Chemistry Research, vol. 46, No. 12, Jun. 1, 2007, pp. 4273-4281.

* cited by examiner

CANCER TREATMENT DELIVERY COMPONENT INCLUDING A CARBON-BASED NANOMATERIAL COMPOSITION, METHOD OF DELIVERING A CANCER TREATMENT DELIVERY COMPONENT INCLUDING A CARBON-BASED NANOMATERIAL COMPOSITION, AND METHODS OF FORMING THE SAME

CROSS-REFERENCE TO RELATED APPLICATION(S)

This application claims priority under 35 U.S.C. § 119(c) to U.S. Provisional Patent Application No. 63/386,210, entitled "CANCER TREATMENT DELIVERY COMPONENT INCLUDING A CARBON-BASED NANOMATERIAL COMPOSITION, METHOD OF DELIVERING A CANCER TREATMENT DELIVERY COMPONENT INCLUDING A CARBON-BASED NANOMATERIAL COMPOSITION, AND METHODS OF FORMING THE SAME," by Evan JOHNSON et al., filed on Dec. 6, 2022, which is assigned to the current assignee hereof and is incorporated herein by reference in its entirety.

FIELD OF THE DISCLOSURE

The present disclosure relates to a cancer treatment delivery component including a carbon-based nanomaterial composition, methods of delivering a cancer treatment delivery component including a carbon-based nanomaterial composition, and methods of forming the same.

SUMMARY

According to a first aspect, a cancer treatment delivery method may include preparing a cancer treatment delivery component that may include a carbon-based nanomaterial composition and a cancer treatment composition attached to the carbon-based nanomaterial composition, delivering the cancer treatment delivery component to a treatment location, and applying a radio frequency to the cancer treatment delivery component at the treatment location. The radio frequency may be configured to heat the cancer treatment delivery component and cause the cancer treatment composition to detach from the carbon-based nanomaterial composition for delivery at the treatment location. The carbon-based nanomaterial composition may include a carbon content of at least about 60% and not greater than about 99% based on elemental analysis of the graphene composition, an oxygen content of at least about 1% and not greater than about 35% based on elemental analysis of the graphene composition, and a nitrogen content of at least about 2% and not greater than 50%.

According to another aspect, a cancer treatment delivery component may include a carbon-based nanomaterial composition and a cancer treatment composition attached to the carbon-based nanomaterial composition. The cancer treatment delivery component may be configured to be delivered to a treatment location and heated using a radio frequency. Heating the cancer treatment delivery component with the radio frequency may cause the cancer treatment composition to detach from the carbon-based nanomaterial composition for delivery at the treatment location. The carbon-based nanomaterial composition may include a carbon content of at least about 60% and not greater than about 99% based on elemental analysis of the graphene composition, an oxygen content of at least about 1% and not greater than about 35% based on elemental analysis of the graphene composition, and a nitrogen content of at least about 2% and not greater than 50%.

According to still another aspect, a method of forming a cancer treatment delivery component may include providing a carbon-based nanomaterial composition, attaching a cancer treatment composition to the carbon-based nanomaterial composition to form the cancer treatment delivery component. The cancer treatment delivery component may be configured to be delivered to a treatment location and heated using a radio frequency. Heating the cancer treatment delivery component with the radio frequency may cause the cancer treatment composition to detach from the carbon-based nanomaterial composition for delivery at the treatment location. The carbon-based nanomaterial composition may include a carbon content of at least about 60% and not greater than about 99% based on elemental analysis of the graphene composition, an oxygen content of at least about 1% and not greater than about 35% based on elemental analysis of the graphene composition, and a nitrogen content of at least about 2% and not greater than about 50%.

BRIEF DESCRIPTION OF THE DRAWINGS

Embodiments are illustrated by way of example and are not limited to the accompanying figures.

Skilled artisans appreciate that elements in the figures are illustrated for simplicity and clarity and have not necessarily been drawn to scale.

DETAILED DESCRIPTION

The following discussion will focus on specific implementations and embodiments of the teachings. The detailed description is provided to assist in describing certain embodiments and should not be interpreted as a limitation on the scope or applicability of the disclosure or teachings. It will be appreciated that other embodiments can be used based on the disclosure and teachings as provided herein.

The terms "comprises," "comprising," "includes," "including," "has," "having" or any other variation thereof, are intended to cover a non-exclusive inclusion. For example, a method, article, or apparatus that comprises a list of features is not necessarily limited only to those features but may include other features not expressly listed or inherent to such method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" is employed to describe elements and components described herein. This is done merely for convenience and to give a general sense of the scope of the invention. This description should be read to include one, at least one, or the singular as also including the plural, or vice versa, unless it is clear that it is meant otherwise. For example, when a single item is described herein, more than one item may be used in place of a single item. Similarly, where more than one item is described herein, a single item may be substituted for that more than one item.

Embodiments described herein are generally directed to a cancer treatment delivery method for delivering a cancer treatment delivery component, a cancer treatment delivery component, and a method of forming a cancer treatment delivery component. According to particular embodiments, the cancer treatment delivery component may include a carbon-based nanomaterial composition and a cancer treatment composition attached to the carbon-based nanomaterial composition. According to other embodiments, the carbon-based nanomaterial composition may be defined as any carbon-based nanomaterial composition that may include a particular carbon content and a particular oxygen content.

Figure 1:
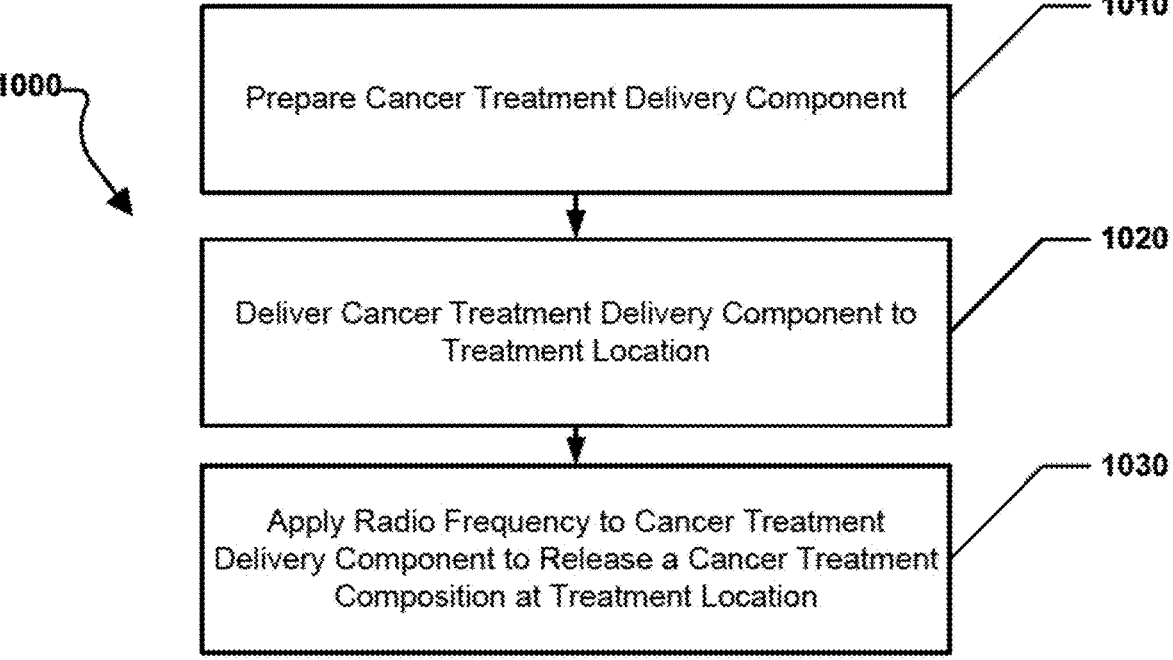
FIG. 1 includes a diagram showing a carbon-based nanomaterial composition forming method according to embodiments described herein.

Referring first to a cancer treatment delivery method for delivering a cancer treatment delivery component, FIG. 1 includes a diagram showing a cancer treatment delivery method 1000 according to embodiments, described herein. According to particular embodiments, the cancer treatment delivery method 1000 may include a first step 1010 of preparing a cancer treatment delivery component, a second step 1020 of delivering the cancer treatment delivery component to a treatment location, and a third step 1030 of applying a radio frequency to the cancer treatment delivery component at the treatment location.

Referring to the first step 1010, the cancer treatment delivery component may include a carbon-based nanomaterial composition and a cancer treatment composition attached to the carbon-based nanomaterial composition.

Referring to the second step 1020, delivery of the cancer treatment delivery component may be accomplished by any known delivery technology, such as injection of the cancer treatment delivery component directly into the bloodstream for transport throughout the body to the treatment location or proximal injection of the cancer treatment delivery component into the body at, or in the general location of, the treatment location.

According to certain embodiments, the treatment location may be any location within, or on the surface of, a body.

Referring to the third step 1030, applying the radio frequency to the cancer treatment delivery component at the treatment location may include the use of any known radio frequency production apparatus, which may be used to direct radio frequency waves at the target location (i.e., direction antenna transmission of radio frequency waves) or may be used to produce radio frequency waves that fill a space encompassing the target location (i.e. non-directional antenna transmission of radio frequency waves).

According to particular embodiments, the radio frequency may be configured to heat the cancer treatment delivery component and cause the cancer treatment composition to detach from the carbon-based nanomaterial composition for delivery at the treatment location.

According to particular embodiments, the radio frequency may include a particular frequency range. For example, the radio frequency may be at least about 100 MHz, such as, at least about 101 MHz or at least about 102 MHz or at least about 103 MHz or at least about 104 MHz or at least about 105 MHz or at least about 106 MHz or at least about 107 MHz or at least about 108 MHz or at least about 109 MHz or at least about 110 MHz or at least about 111 MHZ or at least about 112 MHz or at least about 113 MHz or at least about 114 MHz or at least about 115 MHz or at least about 116 MHz or at least about 117 MHz or at least about 118 MHz or at least about 119 MHz or even at least about 120 MHz. According to still other embodiments, the radio frequency may be not greater than about 140 MHZ, such as, not greater than about 139 MHz or not greater than about 138 MHz or not greater than about 137 MHz or not greater than about 136 MHz or not greater than about 135 MHz or not greater than about 134 MHz or not greater than about 133 MHz or not greater than about 132 MHz or not greater than about 131 MHz or not greater than about 130 MHz or not greater than about 129 MHz or not greater than about 128 MHz or not greater than about 127 MHz or not greater than about 126 MHz or not greater than about 125 MHz or not greater than about 124 MHz or not greater than about 123 MHz or not greater than about 122 MHz or even not greater than about 121 MHz. It will be appreciated that the radio frequency applied to the cancer treatment delivery component may be any value between, and including, any of the minimum and maximum values noted above. It will be further appreciated that the radio frequency applied to the cancer treatment delivery component may be within a range between, and including, any of the minimum and maximum values noted above.

According to still other embodiments, the radio frequency may be transmitted at a particular power. For example, the radio frequency may be transmitted at a power of 1 watt, such as, at least about 1 watt or at least about 5 watts or at least about 10 watts or at least about 50 watts or at least about 100 watts or at least about 150 watts or at least about 200 watts or at least about 250 watts or at least about 300 watts or at least about 350 watts or at least about 400 watts or at least about 450 watts or at least about 500 watts or at least about 750 watts or at least about 1000 watts or at least about 1250 watts or at least about 1500 watts or at least about 1750 watts or even at least about 2000 watts. According to still other embodiments, the radio frequency may be not greater than about 5000 watts, such as, not greater than about 4750 watts or not greater than about 4500 watts or not greater than about 4250 watts or not greater than about 4000 watts or not greater than about 3750 watts or not greater than about 3500 watts or not greater than about 3250 watts or not greater than about 3000 watts or not greater than about 2750 watts or not greater than about 2500 watts or even not greater than about 2250 watts or not greater than about 2000 watts. It will be appreciated that the radio frequency applied to the cancer treatment delivery component may be any value between, and including, any of the minimum and maximum values noted above. It will be further appreciated that the radio frequency applied to the cancer treatment delivery component may be within a range between, and including, any of the minimum and maximum values noted above.

According to still other embodiments, application of the radio frequency may heat the treatment location to a particular temperature. For example, application of the radio frequency may heat the treatment location to a temperature of at least about 50° C., such as, at least about 55° C. or at least about 60° C. or at least about 65° C. or at least about 70° C. or at least about 75° C. or at least about 80° ° C. or at least about 85° C. or at least about 90° C. or at least about 95° C. or at least about 100° ° C. or at least about 105° C. or at least about 110° C. or at least about 115° C. or at least about 120° C. or at least about 125° C. or at least about 130° C. or at least about 135° C. or at least about 140° C. or at least about 145° C. or at least about 150° C. or at least about 155° C. or at least about 160° C. or at least about 165° C. or at least about 170° C. or at least about 175° C. or at least about 180° C. or at least about 185° C. or at least about 190° C. or at least about 195° C. or at least about 200° ° C. or at least about 205° C. or at least about 210° C. or at least about 215° C. or at least about 220° C. or at least about 225° C. or at least about 230° C. or at least about 235° C. or at least about 240° C. or at least about 245° C. or even at least about 250° C. According to still other embodiments, application of the radio frequency may heat the treatment location to a temperature of not greater than about 800° C., such as, not greater than about 750° C. or not greater than about 700° ° C. or not greater than about 650° C. or not greater than about 600° C. or not greater than about 550° C. or not greater than about 500° C. or not greater than about 450° C. or even not greater than about 400° C. It will be appreciated that application of the radio frequency may heat the treatment location to a temperature of any value between, and including, any of the minimum and maximum values noted above. It will be further appreciated that application of the radio frequency may heat the treatment location to a temperature of any value within a range between, and including, any of the minimum and maximum values noted above.

According to still other embodiments, application of the radio frequency may be applied for a particular application time length. For example, the radio frequency application time length may be at least about 0.01 seconds, such as, 0.05 seconds or at least about 0.1 seconds or at least about 0.2 seconds or at least about 0.3 seconds or at least about 0.4 seconds or at least about 0.5 seconds or at least about 0.6 seconds or at least about 0.7 seconds or at least about 0.8 seconds or at least about 0.9 seconds or at least about 1.0 seconds or at least about 5.0 seconds or at least about 10 seconds or at least about 15 seconds or at least about 20 seconds or at least about 25 seconds or even at least about 30 seconds. According to still other embodiments, the radio frequency application time length may be not greater than about 60 seconds, such as, not greater than about 55 seconds or not greater than about 50 seconds or not greater than about 45 seconds or not greater than about 40 seconds or even not greater than about 35 seconds. It will be appreciated that the radio frequency application time length may be any value between, and including, any of the minimum and maximum values noted above. It will be further appreciated that the radio frequency application time length may be any value within a range between, and including, any of the minimum and maximum values noted above.

According to still other embodiments, the radio frequency may be applied in a sequence of bursts, each burst being applied for a particular burst application time length. For example, the radio frequency bust application time length may be at least about 0.01 seconds, such as, 0.05 seconds or at least about 0.1 seconds or at least about 0.2 seconds or at least about 0.3 seconds or at least about 0.4 seconds or at least about 0.5 seconds or at least about 0.6 seconds or at least about 0.7 seconds or at least about 0.8 seconds or at least about 0.9 seconds or at least about 1.0 seconds or at least about 5.0 seconds or at least about 10 seconds or at least about 15 seconds or at least about 20 seconds or at least about 25 seconds or even at least about 30 seconds. According to still other embodiments, the radio frequency burst application time length may be not greater than about 60 seconds, such as, not greater than about 55 seconds or not greater than about 50 seconds or not greater than about 45 seconds or not greater than about 40 seconds or even not greater than about 35 seconds. It will be appreciated that the radio frequency burst application time length may be any value between, and including, any of the minimum and maximum values noted above. It will be further appreciated that the radio frequency burst application time length may be any value within a range between, and including, any of the minimum and maximum values noted above. It will be appreciated that the sequence of busts may be applied for a particular application time length equal to the application time length described herein.

Figure 2:
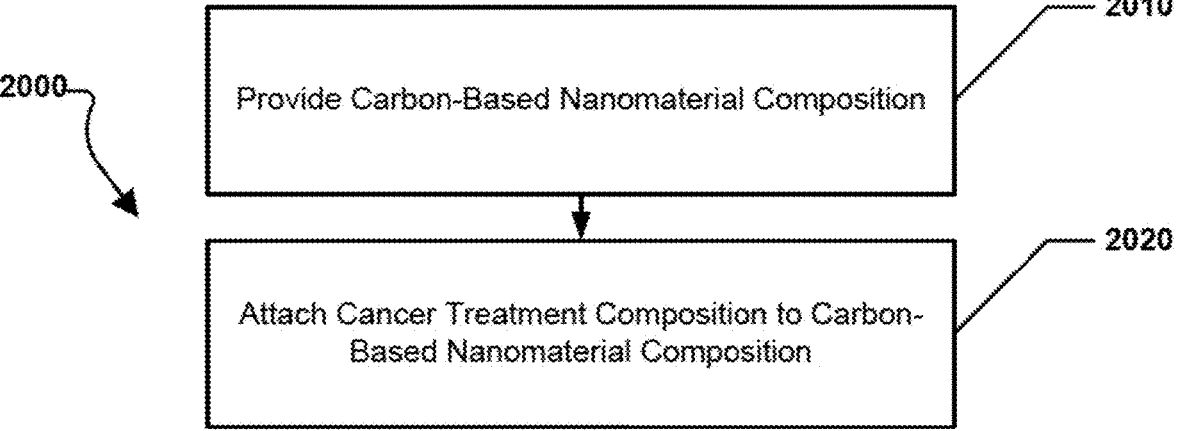
FIG. 2 includes a diagram showing a forming method for forming a cancer treatment delivery component according to embodiments described herein.

Referring now to cancer treatment delivery component according to embodiments described herein. FIG. 2 includes a diagram showing a forming method 2000 for forming a cancer treatment delivery component according to embodiments described herein. According to particular embodiments, the forming method 2000 may include a first step 2010 providing a carbon-based nanomaterial composition, and a second step 2020 of attaching a cancer treatment composition to the carbon-based nanomaterial composition.

Referring to the second step 2020, attaching the cancer treatment composition to the carbon-based nanomaterial composition may be through a functional bond between the cancer treatment composition and the carbon-based nanomaterial composition or through absorption of the cancer treatment composition into the carbon-based nanomaterial. According to still other embodiments, the cancer treatment composition may be absorbed within layers of the carbon-based nanomaterial. For example, if the carbon-based nanomaterial has a sheet structure, the cancer treatment composition may be absorbed within and bond to layers of the sheet structure. According to other embodiments, if the carbon-based nanomaterial has a nano-onion structure, i.e., a structure that includes layers folded over on themselves such that they resemble an onion shell, the cancer treatment composition may be absorbed within and bond to layers of the nano-onion structure.

According to yet other embodiments, the cancer treatment composition may include any cancer treatment, medicine or other molecule designed for delivery at a location within or on the surface of a body for cancer treatment or treatment at a location within or on the surface of a body for cancer treatment.

Figure 3:
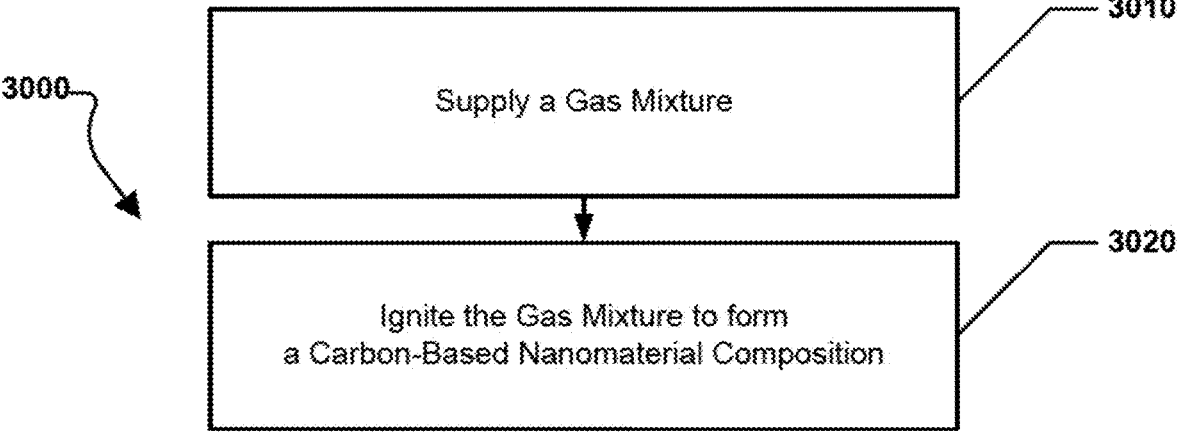
FIG. 3 includes a diagram showing a carbon-based nanomaterial composition forming method according to embodiments described herein.

Referring to first step 2010 of providing a carbon-based nanomaterial composition, FIG. 3 includes a diagram showing a forming method 3000 for forming a carbon-based nanomaterial composition according to embodiments described herein. According to particular embodiments, the forming method 3000 may include a first step 3010 of supplying a gas mixture, and a second step 3020 of igniting the gas mixture to form the carbon-based nanomaterial composition.

Referring to first step 3010, according to particular embodiments, the gas mixture may include acetylene gas, and oxygen gas. According to still other embodiments, the gas mixture may further include hydrogen gas.

According to a certain embodiment, the gas mixture may include a particular molar ratio $AG_{mol}/GM_{mol}$, where the $AG_{mol}$ is equal to the moles of acetylene gas in the gas mixture and $GM_{mol}$ is equal to the total moles of gas in the gas mixture. For example, the gas mixture may include a molar ratio $AG_{mol}/GM_{mol}$ of at least about 0.20, such as, at least about 0.21 or at least about 0.22 or at least about 0.23 or at least about 0.24 or at least about 0.25 or at least about 0.26 or at least about 0.27 or at least about 0.28 or at least about 0.29 or at least about 0.30 or at least about 0.31 or at least about 0.32 or at least about 0.33 or at least about 0.34 or even at least about 0.35. According to still other embodiments, the gas mixture may include a molar ratio $AG_{mol}/$ $GM_{mol}$ of not greater than about 0.99, such as, not greater than about 0.95 or not greater than about 0.90 or not greater than about 0.85 or not greater than about 0.80 or not greater than about 0.75 or not greater than about 0.70 or not greater than about 0.65 or even not greater than about 0.60. It will be appreciated that the gas mixture may include a molar ratio $AG_{mol}/GM_{mol}$ of any value between, and including, any of the minimum and maximum values noted above. It will be further appreciated that the gas mixture may include a molar ratio $AG_{mol}/GM_{mol}$ within a range between, and including, any of the minimum and maximum values noted above.

According to a certain embodiment, the gas mixture may include a particular molar ratio $OG_{mol}/GM_{mol}$, where the $OG_{mol}$ is equal to the moles of oxygen gas in the gas mixture and $GM_{mol}$ is equal to the total moles of gas in the gas mixture. For example, the gas mixture may include a molar ratio $OG_{mol}/GM_{mol}$ of at least about 0.01, such as, at least about 0.02 or at least about 0.03 or at least about 0.04 or at least about 0.05 or at least about 0.06 or at least about 0.07 or at least about 0.08 or at least about 0.09 or at least about 0.10 or even at least about 0.11 or at least about 0.12 or at least about 0.13 or at least about 0.14 or at least about 0.15 or at least about 0.16 or at least about 0.17 or at least about 0.18 or at least about 0.19 or at least about 0.20 or at least about 0.25 or at least about 0.30 or at least about 0.35 or even at least about 0.40. According to still other embodiments, the gas mixture may include a molar ratio $OG_{mol}/GM_{mol}$ of not greater than about 0.85, such as, not greater than about 0.80 or not greater than about 0.75 or not greater than about 0.70 or not greater than about 0.65 or not greater than about 0.60 or not greater than about 0.55 or not greater than about 0.54 or not greater than about 0.53 or not greater than about 0.52 or not greater than about 0.51 or even not greater than about 0.50. It will be appreciated that the gas mixture may include a molar ratio $OG_{mol}/GM_{mol}$ of any value between, and including, any of the minimum and maximum values noted above. It will be further appreciated that the gas mixture may include a molar ratio $OG_{mol}/GM_{mol}$ within a range between, and including, any of the minimum and maximum values noted above.

According to a certain embodiment, the gas mixture may include a particular molar ratio $HG_{mol}/GM_{mol}$, where the $HG_{mol}$ is equal to the moles of hydrogen gas in the gas mixture and $GM_{mol}$ is equal to the total moles of gas in the gas mixture. For example, the gas mixture may include a molar ratio $HG_{mol}/GM_{mol}$ of at least about 0.05, such as, at least about 0.10 or at least about 0.15 or at least about 0.20 or at least about 0.25 or at least about 0.30 or even at least about 0.35. According to still other embodiments, the gas mixture may include a molar ratio $HG_{mol}/GM_{mol}$ of not greater than about 0.99, such as, not greater than about 0.95 or not greater than about 0.90 or not greater than about 0.85 or not greater than about 0.80 or not greater than about 0.75 or not greater than about 0.70 or not greater than about 0.65 or not greater than about 0.60 or not greater than about 0.55 or not greater than about 0.50 or not greater than about 0.45 or even not greater than about 0.40. It will be appreciated that the gas mixture may include a molar ratio $HG_{mol}/GM_{mol}$ of any value between, and including, any of the minimum and maximum values noted above. It will be further appreciated that the gas mixture may include a molar ratio $HG_{mol}/GM_{mol}$ within a range between, and including, any of the minimum and maximum values noted above.

According to a certain embodiment, the gas mixture may further include methane gas. According to still other embodiments, the gas mixture may include a particular molar ratio $MG_{mol}/GM_{mol}$, where the $MG_{mol}$ is equal to the moles of methane gas in the gas mixture and $GM_{mol}$ is equal to the total moles of gas in the gas mixture. For example, the gas mixture may include a molar ratio $MG_{mol}/GM_{mol}$ of at least about 0.25, such as, at least about 0.26 or at least about 0.27 or at least about 0.28 or at least about 0.29 or at least about 0.30 or at least about 0.31 or at least about 0.32 or at least about 0.33 or at least about 0.34 or even at least about 0.35. According to still other embodiments, the gas mixture may include a molar ratio $MG_{mol}/GM_{mol}$ of not greater than about 0.99, such as, not greater than about 0.95 or not greater than about 0.90 or not greater than about 0.85 or not greater than about 0.80 or not greater than about 0.75 or not greater than about 0.70 or not greater than about 0.65 or even not greater than about 0.60. It will be appreciated that the gas mixture may include a molar ratio $MG_{mol}/GM_{mol}$ of any value between, and including, any of the minimum and maximum values noted above. It will be further appreciated that the gas mixture may include a molar ratio $MG_{mol}/GM_{mol}$ within a range between, and including, any of the minimum and maximum values noted above.

According to particular embodiments, the gas mixture may include a particular content of acetylene gas. For example, the gas mixture may include acetylene gas at a concentration of at least about 1.2 mol, such as, at least about 1.4 mol or at least about 1.6 mol or at least about 1.8 mol or at least about 2.0 mol or at least about 2.05 mol or at least about 2.06 mol or at least about 2.07 mol or at least about 2.08 mol or at least about 2.09 mol or at least about 2.10 mol or at least about 2.11 mol or at least about 2.12 mol or at least about 2.13 mol or at least about 2.14 mol or at least about 2.15 mol or at least about 2.16 mol or at least about 2.17 mol or at least about 2.18 mol or at least about 2.19 mol or at least about 2.20 mol or at least about 2.25 mol or at least about 2.30 mol or at least about 2.35 mol or at least about 2.40 mol or at least about 2.45 mol or at least about 2.50 mol or at least about 2.75 mol or at least about 3.0 mol or at least about 3.5 mol or at least about 4.0 mol or at least about 4.5 mol or at least about 5.0 mol or at least about 5.5 mol or at least about 6.0 mol or even at least about 6.5 mol. According to still other embodiments, the gas mixture may include acetylene gas at a concentration of not greater than about 18.0 mol, such as, not greater than about 17.0 mol or not greater than about 16.0 mol or not greater than about 15.0 mol or not greater than about 14.0 mol or not greater than about 13.0 mol or not greater than about 12.0 mol or not greater than about 11.0 mol or not greater than about 10.0 mol or not greater than about 9.0 mol or even not greater than about 8.0 mol. It will be appreciated that the acetylene gas concentration in the gas mixture may be any value between, and including, any of the minimum and maximum values noted above. It will be further appreciated that the acetylene gas concentration in the gas mixture may be within a range between, and including, any of the minimum and maximum values noted above.

According to other embodiments, the gas mixture may include a particular content of oxygen gas. For example, the gas mixture may include oxygen gas at a concentration of at least about 0.3 mol, such as, at least about 0.31 mol or at least about 0.32 mol or at least about 0.33 mol or at least about 0.34 mol or at least about 0.35 mol or at least about 0.36 mol or at least about 0.37 mol or at least about 0.38 mol or at least about 0.39 mol or at least about 0.40 mol or at least about 0.41 mol or at least about 0.42 mol or at least about 0.43 mol or at least about 0.44 mol or at least about 0.45 mol or at least about 0.46 mol or at least about 0.47 mol or at least about 0.48 mol or even at least about 0.49 mol. According to still other embodiments, the gas mixture may include oxygen gas at a concentration of not greater than about 12 mol, such as, not greater than about 10 mol or not greater than about 8.0 mol or not greater than about 6.0 mol or not greater than about 4.0 mol or not greater than about 2.0 mol or not greater than about 1.0 mol or not greater than about 0.75 mol or even not greater than about 0.5 mol. It will be appreciated that the oxygen gas concentration in the gas mixture may be any value between, and including, any of the minimum and maximum values noted above. It will be further appreciated that the oxygen gas concentration in the gas mixture may be within a range between, and including, any of the minimum and maximum values noted above.

According to still other embodiments, the gas mixture may include a particular content of hydrogen gas. For example, the gas mixture may include hydrogen gas at a concentration of at least about 0.60 mol, such as, at least about 0.61 mol or at least about 0.62 mol or at least about 0.63 mol or at least about 0.64 mol or at least about 0.65 mol or at least about 0.66 mol or at least about 0.67 mol or at least about 0.68 mol or at least about 0.69 mol or at least about 0.70 mol or at least about 0.71 mol or at least about 0.72 mol or at least about 0.73 mol or at least about 0.74 mol or at least about 0.75 mol or at least about 0.76 mol or at least about 0.77 mol or at least about 0.78 mol or at least about 0.79 mol or even at least about 0.80 mol. According to still other embodiments, the gas mixture may include hydrogen gas at a concentration of not greater than about 20.0 mol, such as, not greater than about 15 mol or not greater than about 10.0 mol or not greater than about 5.0 mol or not greater than about 4.0 mol or not greater than about 3.5 mol or not greater than about 3.0 mol or not greater than about 2.5 mol or not greater than about 2.0 mol or not greater than about 1.5 mol or even not greater than about 1.0 mol. It will be appreciated that the hydrogen gas concentration in the gas mixture may be any value between, and including, any of the minimum and maximum values noted above. It will be further appreciated that the hydrogen gas concentration in the gas mixture may be within a range between, and including, any of the minimum and maximum values noted above.

According to particular embodiments, the gas mixture may include a particular content of methane gas. For example, the gas mixture may include methane gas at a concentration of at least about 1.2 mol, such as, at least about 1.4 mol or at least about 1.6 mol or at least about 1.8 mol or at least about 2.0 mol or at least about 2.05 mol or at least about 2.06 mol or at least about 2.07 mol or at least about 2.08 mol or at least about 2.09 mol or at least about 2.10 mol or at least about 2.11 mol or at least about 2.12 mol or at least about 2.13 mol or at least about 2.14 mol or at least about 2.15 mol or at least about 2.16 mol or at least about 2.17 mol or at least about 2.18 mol or at least about 2.19 mol or at least about 2.20 mol or at least about 2.25 mol or at least about 2.30 mol or at least about 2.35 mol or at least about 2.40 mol or at least about 2.45 mol or at least about 2.50 mol or at least about 2.75 mol or at least about 3.0 mol or at least about 3.5 mol or at least about 4.0 mol or at least about 4.5 mol or at least about 5.0 mol or at least about 5.5 mol or at least about 6.0 mol or even at least about 6.5 mol. According to still other embodiments, the gas mixture may include methane gas at a concentration of not greater than about 18.0 mol, such as, not greater than about 17.0 mol or not greater than about 16.0 mol or not greater than about 15.0 mol or not greater than about 14.0 mol or not greater than about 13.0 mol or not greater than about 12.0 mol or not greater than about 11.0 mol or not greater than about 10.0 mol or not greater than about 9.0 mol or even not greater than about 8.0 mol. It will be appreciated that the methane gas concentration in the gas mixture may be any value between, and including, any of the minimum and maximum values noted above. It will be further appreciated that the methane gas concentration in the gas mixture may be within a range between, and including, any of the minimum and maximum values noted above.

Referring now to embodiments of the carbon-based nanomaterial composition formed according to forming method 100, the carbon-based nanomaterial composition may include particular carbon content based on elemental analysis conducted using x-ray photoelectron spectroscopy (XPS). For example, the carbon-based nanomaterial composition may include a carbon content of at least about 75.0%, such as, at least about 78.0% or at least about 80.0% or at least about 83% or at least about 85% or at least about 88% or at least about 90% or at least about 91% or at least about 92% or at least about 93% or at least about 94.0% or even at least about 95.0%. According to still other embodiments, the carbon-based nanomaterial composition may include a carbon content of not greater than about 100%, such as, not greater than about 99.5% or not greater than about 99% or not greater than about 98.5% or not greater than about 98% or not greater than about 97.5% or not greater than about 97% or not greater than about 96.5% or even not greater than about 96.0%. It will be appreciated that the carbon content in the carbon-based nanomaterial composition may be any value between, and including, any of the minimum and maximum values noted above. It will be further appreciated that the carbon content in the carbon-based nanomaterial composition may be within a range between, and including, any of the minimum and maximum values noted above.

According to still other embodiments, the carbon-based nanomaterial composition may include particular oxygen content based on elemental analysis conducted using x-ray photoelectron spectroscopy (XPS). For example, the carbon-based nanomaterial composition may include an oxygen content of at least about 0.0%, such as, at least about 0.5% or at least about 1.0% or at least about 1.5% or at least about 2.0% or at least about 2.5% or at least about 3.0% or at least about 3.5% or at least about 4.0% or at least about 4.5% or even at least about 5.0%. According to still other embodiments, the carbon-based nanomaterial composition may include an oxygen content of not greater than about 25%, such as, not greater than about 23% or not greater than about 20% or not greater than about 18% or not greater than about 15% or not greater than about 13% or not greater than about 10% or not greater than about 8% or even not greater than about 6.0%. It will be appreciated that the oxygen content in the carbon-based nanomaterial composition may be any value between, and including, any of the minimum and maximum values noted above. It will be further appreciated that the oxygen content in the carbon-based nanomaterial composition may be within a range between, and including, any of the minimum and maximum values noted above.

According to still other embodiments, the carbon-based nanomaterial composition may have a particular D/G ratio as measured by performing x-ray photoelectron spectroscopy on a sample of powder and detangling the spectrum produced. For example, the carbon-based nanomaterial composition may have a D/G ratio of at least about 0.1, such as, at least about 0.15 or at least about 0.20 or at least about 0.25 or at least about 0.30 or at least about 0.35 or at least about 0.40 or at least about 0.45. According to still other embodiments, the carbon-based nanomaterial composition may have a D/G ratio of not greater than about 2.0, such as, not greater than about 1.95 or not greater than about 1.90 or not greater than about 1.85 or not greater than about 1.80 or not greater than about 1.75 or not greater than about 1.70 or not greater than about 1.65 or not greater than about 1.60 or not greater than about 1.55 or not greater than about 1.50 or not greater than about 1.45 or not greater than about 1.40 or not greater than about 1.35 or not greater than about 1.30 or not greater than about 1.25 or not greater than about 1.20 or not greater than about 1.15 or not greater than about 1.10 or not greater than about 1.05 or not greater than about 1.00 or not greater than about 0.95 or not greater than about 0.9 or not greater than about 0.85 or not greater than about 0.8 or not greater than about 0.75 or not greater than about 0.7 or not greater than about 0.65 or even not greater than about 0.6. It will be appreciated that the D/G ratio of the carbon-based nanomaterial composition may be any value between, and including, any of the minimum and maximum values noted above. It will be further appreciated that the D/G ratio of the carbon-based nanomaterial composition may be within a range between, and including, any of the minimum and maximum values noted above.

According to still other embodiments, the carbon-based nanomaterial composition may have a particular aspect ratio as measured by dividing the lateral size by the thickness of a given sample. For example, the carbon-based nanomaterial composition may have an aspect ratio of at least about 1.0, such as, at least about 5 or at least about 10 or at least about 15. According to still other embodiments, the carbon-based nanomaterial composition may have an aspect ratio of not greater than about 100, such as, not greater than about 95 or not greater than about 90 or not greater than about 85 or not greater than about 80 or not greater than about 75 or not greater than about 70 or not greater than about 65 or even not greater than about 60. It will be appreciated that the aspect ratio of the carbon-based nanomaterial composition may be any value between, and including, any of the minimum and maximum values noted above. It will be further appreciated that the aspect ratio of the carbon-based nanomaterial composition may be within a range between, and including, any of the minimum and maximum values noted above.

According to yet other embodiments, the carbon-based nanomaterial composition may have a particular carbon hybridization ratio $P_{sp3}/P_{sp2}$, where $P_{sp3}$ is the percent of carbon within the carbon-based nanomaterial composition having a sp3 hybridization and $P_{sp2}$ is the percent of carbon within the carbon-based nanomaterial composition having a sp2 hybridization. For example, the carbon-based nanomaterial composition may have a carbon hybridization ratio $P_{sp3}/P_{sp2}$ of at least about 0.0, such as, at least about 0.1 or at least about 0.2 or at least about 0.3 or at least about 0.4 or at least about 0.5 or at least about 0.6 or at least about 0.7 or at least about 0.8 or at least about 0.9 or at least about 1.0 or at least about 1.1 or at least about 1.2 or at least about 1.3 or at least about 1.4 or even at least about 1.5. According to still other embodiments, the carbon-based nanomaterial composition may have a carbon hybridization ratio $P_{sp3}/P_{sp2}$ of not greater than about 5.00, such as, not greater than about 4.75 or not greater than about 4.5 or not greater than about 4.25 or not greater than about 4.0 or not greater than about 3.75 or not greater than about 3.50 or not greater than about 3.25 or not greater than about 3.0 or not greater than about 2.9 or not greater than about 2.8 or not greater than about 2.7 or not greater than about 2.6 or not greater than about 2.5 or not greater than about 2.4 or not greater than about 2.3 or not greater than about 2.2 or not greater than about 2.1 or even not greater than about 2.0. It will be appreciated that the carbon hybridization ratio $P_{sp3}/P_{sp2}$ of the carbon-based nanomaterial composition may be any value between, and including, any of the minimum and maximum values noted above. It will be further appreciated that the carbon hybridization ratio $P_{sp3}/P_{sp2}$ of the carbon-based nanomaterial composition may be within a range between, and including, any of the minimum and maximum values noted above.

According to certain embodiments, the carbon-based nanomaterial composition may have particular carbon structures. For example, according to certain embodiments, the carbon-based nanomaterial composition may include carbon-based nanosheets. According to certain embodiments, the carbon-based nanomaterial composition may consist of carbon-based nanosheets. For purposes of embodiments described herein, a nanosheet may be defined as a two-dimensional allotropic form of carbon. According to still other embodiments, a nanosheet may have Sp2-hybridized carbon atoms, connected by sigma and pi bonds in a hexagonal lattice of polyaromatic rings.

According to certain embodiments, the carbon-based nanomaterial composition may include carbon-based nano-flakes. According to certain embodiments, the carbon-based nanomaterial composition may consist of carbon-based nanoflakes. For purposes of embodiments described herein, a nanoflake may be defined as a Lamellae of graphene, such as, a two-dimensional carbon sheet. According to still other embodiments, the nanoflakes may have a two-dimensional carbon sheet size of between about 50 nm and 100 nm.

According to certain embodiments, the carbon-based nanomaterial composition may include carbon-based nano-spheres. According to certain embodiments, the carbon-based nanomaterial composition may consist of carbon-based nanospheres. For purposes of embodiments described herein, a nanosphere may be defined as a Sp2-hybridized form of carbon with atomic carbon clusters formed into a spherical structure via covalent bonds. According to certain embodiments, the nanospheres can have radii ranging from about 50 nm to about 250 nm.

According to certain embodiments, the carbon-based nanomaterial composition may include carbon-based nano-onions. According to certain embodiments, the carbon-based nanomaterial composition may consist of carbon-based nano-onions. For purposes of embodiments described herein, a nano-onion may be defined as a nanostructure that includes multiple concentric shells of hexagonal-latticed sheets, strained to form spherical structures. According to still other embodiments, the nano-onions may include layers folded over on themselves such that they resemble an onion shell, sometimes encompassing a small volume of amorphous carbon.

According to still other embodiments, the carbon-based nanomaterial composition may include carbon black. According to certain embodiments, the carbon-based nanomaterial composition may consist of carbon black. For purposes of embodiments described herein, carbon black may be defined as material that is spherical with radii below 1000 nm. According to still other embodiments, the carbon black may be amorphous and may be a black fine powder.

According to still other embodiments, the carbon-based nanomaterial composition may include turbostratic carbon. According to certain embodiments, the carbon-based nanomaterial composition may consist of turbostratic carbon. For purposes of embodiments described herein, turbostratic carbon may be defined as a material having a mixture of sp2- and sp3-hybridized carbon, where the sp2-hybridized planes are surrounded and connected by a sp3-hybridized amorphous matrix. The turbostratic carbon may include curved sheets of graphene-like carbon-polyaromatic structures, forming grape-like fractal aggregates of primary particles.

According to still other embodiments, the carbon-based nanomaterial composition may include any combination of carbon-based nanosheets, carbon-based nanoflakes, carbon-based nanospheres, carbon-based nano-onions, carbon black, or turbostratic carbon. According to still other embodiments, the carbon-based nanomaterial composition may consist of any combination of carbon-based nanosheets, carbon-based nanoflakes, carbon-based nanospheres, carbon-based nano-onions, carbon black, or turbostratic carbon.

Figure 4:
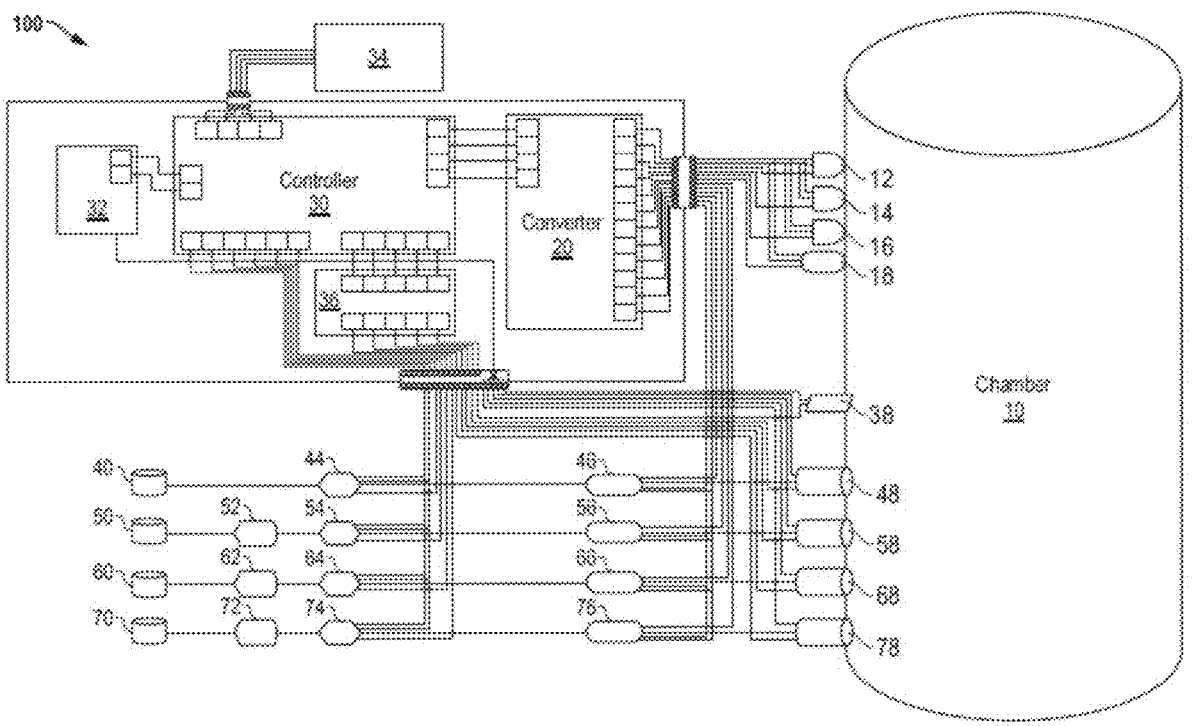
FIG. 4 includes a schematic diagram of a carbon capture system according to an embodiment of the present disclosure.

Turning now to a system for synthesis of carbon-based nanomaterial composition according to embodiments described herein, FIG. 4 includes a diagram of a carbon capture system according to embodiments described herein. As shown in FIG. 4, a carbon capture system 100 according to embodiments of the present disclosure includes a combustion chamber 10 for conversion of hydrocarbon gas or liquid into carbon-based nanomaterial composition. The system 100 may be scaled as needed and may be located onsite, for example, at a hydrocarbon drilling operation or other suitable hydrocarbon feedstock site. Advantageously, the apparatus and methods disclosed herein permit a wide range of hydrocarbons to be used as a feedstock thereby converting numerous types of carbon-containing fluids, such as industrial flue gas output, to generate a valuable product, e.g., carbon-based nanomaterial composition. Thus, the disclosure herein beneficially teaches to capture a variety of carbon in industrial outputs and minimize greenhouse gas emissions therefrom while providing a valuable product for further industrial processes, materials, and equipment, for example, carbon-based nanomaterial composition-coated proton electron membranes. The combustion chamber 10 of FIG. 4 may be a heavy-duty chamber with multiple injection ports for controlled injection of the hydrocarbon material and separate injection of oxygen and hydrogen that forces re-bonding of carbon, hydrogen, and oxygen when ignited to form carbon-based nanomaterial composition and other products that do not contribute to greenhouse gas emissions, such as water. Without being bound by theory, the use of controlled, separate injection of oxygen and hydrogen allows for a much faster combustion of the hydrocarbon material as compared with traditional oxidizing agents; this permits a more complete breakdown of the hydrocarbon material. The combustion chamber 10 may be formed of any suitable material, such as aluminum, titanium aluminum, nickel aluminum, cast iron, steel, and the like. In some embodiments, the combustion chamber 10 is configured to withstand at least 1000 psi of internal pressure.

The combustion chamber 10 may include one or more sensors configured to monitor and measure conditions within the combustion chamber 10. In some embodiments, the combustion chamber 10 includes a temperature sensor 18 configured to measure a temperature within the combustion chamber 10. In some embodiments, the combustion chamber 10 includes a low pressure sensor 16, a pressure sensor 14, and a high pressure sensor 12, each configured to measure a pressure within the combustion chamber 10. In one or more embodiments, the combustion chamber 10 may include an opacity sensor configured to measure an opacity within the combustion chamber 10. In some embodiments, the combustion chamber 10 may include a vacuum valve configured to create a vacuum within the combustion chamber 10 as a precursor to introducing any reactants (or inert gas). In some embodiments, the combustion chamber 10 includes a pressure release valve configured to release pressure from the combustion chamber 10. The pressure release valve may be actuated once a threshold pressure is reached within the combustion chamber 10 and/or on demand, for example, at a set time after each combustion within the combustion chamber 10.

The system includes an inert gas source 40, a flue gas source 50, an oxygen source 60, and a hydrogen source 70 each in fluidic communication with the combustion chamber 10. The inert gas source 40 is arranged to provide a supply of an inert gas, such as argon, under pressure to the combustion chamber 10, wherein said pressure may be monitored by a pressure sensor 44. The inert gas provides an inert environment for clean combustion within the combustion chamber 10. For instance, the inert environment may prevent or suppress formation of NOx (nitrogen oxides) that might otherwise occur. A flow meter 46 is provided between the inert gas source 40 and the combustion chamber 10 and the flow meter 46 is configured to measure a flow rate of inert gas from the inert gas source 40 into the combustion chamber 10. The inert gas is introduced into the combustion chamber 10 through an injection port 48, which may include a one-way valve in order to maintain pressure within the combustion chamber 10 and avoid flashback. In some embodiments, the one-way valve is a solenoid valve.

The flue gas source 50 supplies a carbon-based gas or liquid to the combustion chamber 10. Suitable carbon-based gases or liquids include a variety of commercial and industrial output products that include carbon, typically in a hydrocarbon, which include but are not limited to carbon dioxide, methane, propane, acetylene, butane, or combinations thereof. The carbon content of the carbon-based gases or liquids is not particularly limited. In some embodiments, the flue gas source 50 is an exhaust stream from an industrial reaction process, such as a coal energy plant, a drilling operation, a combustion engine, or a landfill. In other embodiments, the exhaust stream from said industrial reaction process may be collected and stored in a tank or other vessel that may be used later in the system 100. In some embodiments, the flue gas source 50 comprises a holding tank configured to receive and pressurize the exhaust stream from such an industrial process to provide a consistent feedstock pressure to the apparatus herein. In any embodiment, the flue gas source 50 may include a pressure sensor 54 in communication therewith configured to monitor a pressure of the carbon-based gas or liquid from the flue gas source 50. Between the flue gas source 50 and the combustion chamber 10 is a flow meter 56 configured to measure a flow rate of the carbon-based gas or liquid from the flue gas source 50 into the combustion chamber 10. The carbon-based gas or liquid is introduced into the combustion chamber 10 through an injection port 58, which may include a one-way valve in order to maintain pressure within the combustion chamber 10 and avoid flashback. In some embodiments, the one-way valve is a solenoid valve. In some embodiments, a flash arrester 52 may also be included between the flue gas source 50 and the combustion chamber 10, e.g., between the pressure sensor 54 and the flue gas source 50. The flash arrester 52 may include a sensor configured to detect flashback during the combustion process in the combustion chamber 10 and, in response, shut down the system 100 to minimize or avoid the risk of explosion or fire.

The oxygen source 60 supplies oxygen gas to the combustion chamber 10. In some embodiments, the oxygen source 60 is pressurized at about 50 psi or greater. In some embodiments, the oxygen source 60 receives oxygen from a proton exchange membrane (PEM) electrolyzer and, optionally, pressurizes the oxygen. In other embodiments, the oxygen source 60 comprises an oxygen cylinder. In any embodiment, the oxygen source 60 may include a pressure sensor 64 in communication therewith configured to monitor a pressure of the oxygen from the oxygen source 60. Between the oxygen source 60 and the combustion chamber 10 is a flow meter 66 configured to measure a flow rate of the oxygen from the oxygen source 60 into the combustion chamber 10. The oxygen is introduced into the combustion chamber 10 through an injection port 68, which may include a one-way valve in order to maintain pressure within the combustion chamber 10 and avoid flashback. In some embodiments, the one-way valve is a solenoid valve. In some embodiments, a flash arrester 62 may also be included between the oxygen source 60 and the combustion chamber 10, e.g., between the pressure sensor 64 and the oxygen source 60. The flash arrester 62 may include a sensor configured to detect flashback during the combustion process in the combustion chamber 10 and, in response, shut down the system 100.

The hydrogen source 70 supplies hydrogen gas to the combustion chamber 10. In some embodiments, the hydrogen source 70 is pressurized at about 50 psi or greater. In some embodiments, the hydrogen source 70 receives hydrogen from a proton exchange membrane (PEM) electrolyzer and, optionally, pressurizes the hydrogen. In other embodiments, the hydrogen source 70 comprises a hydrogen cylinder. In any embodiment, the hydrogen source 70 may include a pressure sensor 74 in communication therewith configured to monitor a pressure of the hydrogen from the hydrogen source 70. Between the hydrogen source 70 and the combustion chamber 10 is a flow meter 76 configured to measure a flow rate of the hydrogen from the hydrogen source 70 into the combustion chamber 10. The hydrogen is introduced into the combustion chamber 10 through an injection port 78, which may include a one-way valve in order to maintain pressure within the combustion chamber 10 and avoid flashback. In some embodiments, the one-way valve is a solenoid valve. In some embodiments, a flash arrester 72 may also be included between the hydrogen source 70 and the combustion chamber 10, e.g., between the pressure sensor 74 and the hydrogen source 70. The flash arrester 72 may include a sensor configured to detect flashback during the combustion process in the combustion chamber 10 and, in response, shut down the system 100.

The combustion chamber 10 includes an ignition device 38, such as a spark plug. The ignition device 38 is configured to initiate a series of precisely timed combustions. For example, each combustion event may last about a millisecond. The spacing between combustions and the duration of combustions may be appropriately adjusted based on the measured conditions of the system 100. In one or more embodiments, the ignition device 38 is positioned at a mid-point of the combustion chamber 10. According to this configuration, as particles of the reactants (flue gas, oxygen, and hydrogen) accelerate in each direction the particles hit at each end and assemble the carbon-based nanomaterial composition.

The system 100 also includes a controller 30 configured to receive inputs from the sensors within the system 100 and to control combustion conditions within the combustion chamber 10. In some embodiments, the controller 30 in configured to receive inputs from one or more of the flow meters 46, 56, 66, 76, the temperature sensor 18, the low pressure sensor 16, the pressure sensor 14, the high pressure sensor 12, and the pressure sensors 44, 54, 64, 74. In some embodiments, the controller 30 comprises a converter 20 configured to receive said inputs as analog signals and convert the analog signals into digital signals.

The controller 30 may also include a driver 36. In some embodiments, the driver 36 is configured to actuate one or more of the solenoid valves at injection ports 48, 58, 68, 78 and/or to actuate the ignition device 38. In some embodiments, the controller 30 may also include a power distributor 32 to distribute power throughout the system, for example, to the solenoid valves at injection ports 48, 58, 68, 78 and to the ignition device 38.

In one or more embodiments, the system 100 includes a user interface 34. The user interface 34 may display any one or more of the measurements from the sensors described above. In some embodiments, the user interface 34 may be configured to allow customization of the combustion conditions, such as flow rates, pressure, and temperature. The user interface 34 may allow for individual control of each parameter of the system 100 and/or may include pre-programmed functions.

In one or more embodiments, the combustion chamber 10 is maintained at about 100°F or less before combustion, which helps build pressure once carbon-based nanomaterial composition is produced. After combustion, the temperature within the combustion chamber 10 may be around about 120°F. In some embodiments, a pressure within the combustion chamber 10 is maintained at about 5 to 20 psi prior to combustion. In some embodiments, a pressure within the combustion chamber 10 before combustion is about one half that of a pressure after combustion, for example to about 10 to 40 psi, to facilitate efficient conversion of the carbon-based flue gas into carbon-based nanomaterial composition production.

In some embodiments, the system 100 may be automated to achieve a cost-efficient carbon-based nanomaterial composition production method on- or off-site. The automated system 100 determines the mixture for each internal combustion in the chamber to produce carbon-based nanomaterial composition in real time. In other embodiments, through the use of the user interface 34, the system 100 may be manually controlled.

In any embodiment, the system 100 may be configured to measure, in real-time, the make-up of the carbon-based gas or liquid. Such a measurement may be, for example, derived from the measured temperature and pressure changes within the combustion chamber 10 during and after combustion. The ratios of the carbon-based gas or liquid, hydrogen, and oxygen may be precisely adjusted to achieve a consistent carbon-based nanomaterial composition product, to modify the conversion of carbon from the carbon-based feedstock into carbon-based nanomaterial composition to increase the yield thereof, or ideally, both. After each combustion, the system 100 makes small adjustments as needed to one or more parameters to improve the efficiency of carbon-based nanomaterial composition production. A number of combustions may be required to reach optimal combustion conditions for a given carbon-based gas or liquid. However, the precise control of each of the input reactants allows the system 100 to operate with a wide range of carbon sources-even with a variable carbon source.

Referring now to alternative embodiments, the cancer treatment delivery component may further include a cancer cell targeting composition attached to the carbon-based nanomaterial composition. According to particular embodiments, the cancer cell targeting composition may include any molecule that is specifically attracted to cancer cells. According to certain embodiments, the cancer cell targeting composition may be coated onto the surface of the carbon-based nanomaterial composition or absorbed in the carbon-based nanomaterial. According to still other embodiments, the cancer cell targeting composition may act to guide the cancer treatment delivery component to the treatment location for delivery of the cancer treatment delivery component.

Many different aspects and embodiments are possible. Some of those aspects and embodiments are described herein. After reading this specification, skilled artisans will appreciate that those aspects and embodiments are only illustrative and do not limit the scope of the present invention. Embodiments may be in accordance with any one or more of the embodiments as listed below.

Embodiment 1. A cancer treatment delivery method comprising: preparing a cancer treatment delivery component comprising a carbon-based nanomaterial composition and a cancer treatment composition attached to the carbon-based nanomaterial composition; delivering the cancer treatment delivery component to a treatment location; and applying a radio frequency to the cancer treatment delivery component at the treatment location, wherein the radio frequency is configured to heat the cancer treatment delivery component and cause the cancer treatment composition to detach from the carbon-based nanomaterial composition for delivery at the treatment location, wherein the carbon-based nanomaterial composition comprises: a carbon content of at least about 60% and not greater than about 99% based on elemental analysis of the graphene composition, an oxygen content of at least about 1% and not greater than about 35% based on elemental analysis of the graphene composition, and a nitrogen content of at least about 2% and not greater than 50%.

Embodiment 2. A cancer treatment delivery component comprising: a carbon-based nanomaterial composition and a cancer treatment composition attached to the carbon-based nanomaterial composition; wherein the cancer treatment delivery component is configured to be delivered to a treatment location and heated using a radio frequency at the treatment location, wherein heating the cancer treatment delivery component causes the cancer treatment composition to detach from the carbon-based nanomaterial composition for delivery at the treatment location, wherein the carbon-based nanomaterial composition comprises: a carbon content of at least about 60% and not greater than about 99% based on elemental analysis of the graphene composition, an oxygen content of at least about 1% and not greater than about 35% based on elemental analysis of the graphene composition, and a nitrogen content of at least about 2% and not greater than 50%.

Embodiment 3. A method of forming a cancer treatment delivery component, wherein the method comprises: providing a carbon-based nanomaterial composition, and attaching a cancer treatment composition to the carbon-based nanomaterial composition to form the cancer treatment delivery component, wherein the cancer treatment delivery component is configured to be delivered to a treatment location and heated using a radio frequency at the treatment location, wherein heating the cancer treatment delivery component causes the cancer treatment composition to detach from the carbon-based nanomaterial composition, wherein the carbon-based nanomaterial composition comprises: a carbon content of at least about 60% and not greater than about 99% based on elemental analysis of the graphene composition, an oxygen content of at least about 1% and not greater than about 35% based on elemental analysis of the graphene composition, and a nitrogen content of at least about 2% and not greater than about 50%.

Embodiment 4. The cancer treatment delivery method, cancer treatment delivery component, or method of forming a cancer treatment delivery component of any one of embodiments 1, 2, and 3, wherein the cancer treatment composition comprises a cancer treatment, medicine or other molecule designed for delivery at a location within or on the surface of a body for cancer treatment or treatment at a location within or on the surface of a body for cancer treatment.

Embodiment 5. The cancer treatment delivery method, cancer treatment delivery component, or method of forming a cancer treatment delivery component of any one of embodiments 1, 2, and 3, wherein the treatment location comprises a cancer treatment, medicine or other molecule designed for delivery at a location within or on the surface of a body for cancer treatment or treatment at a location within or on the surface of a body for cancer treatment.

Embodiment 6. The cancer treatment delivery method, cancer treatment delivery component, or method of forming a cancer treatment delivery component of any one of embodiments 1, 2, and 3, wherein the radio frequency applied to the treatment location is at least about 100 MHZ.

Embodiment 7. The cancer treatment delivery method, cancer treatment delivery component, or method of forming a cancer treatment delivery component of any one of embodiments 1, 2, and 3, wherein the carbon-based nanomaterial composition is formed by a method comprising: supplying a gas mixture comprising: acetylene gas at a molar ratio $AG_{mol}/GM_{mol}$ of at least about 0.20 and not greater than about 0.99, where the $AG_{mol}$ is equal to the moles of acetylene gas in the gas mixture and $GM_{mol}$ is equal to the total moles of gas in the gas mixture, oxygen gas at a molar ratio $OG_{mol}/GM_{mol}$ of at least about 0.01 and not greater than about 0.85, where the $OG_{mol}$ is equal to the moles of oxygen gas in the gas mixture and $GM_{mol}$ is equal to the total moles of gas in the gas mixture, and hydrogen gas at a molar ratio $HG_{mol}/GM_{mol}$ of at least about 0.05 and not greater than about 0.99, where the $HG_{mol}$ is equal to the moles of hydrogen gas in the gas mixture and $GM_{mol}$ is equal to the total moles of gas in the gas mixture, igniting the gas mixture to form the carbon-based nanomaterial composition, wherein the carbon-based nanomaterial composition has a carbon hybridization ratio $P_{sp3}/P_{sp2}$ of at least about 0.0 and not greater than about 5.0, where $P_{sp3}$ is the percent of carbon within the carbon-based nanomaterial composition having a sp3 hybridization and $P_{sp2}$ is the percent of carbon within the carbon-based nanomaterial composition having a sp2 hybridization.

Embodiment 8. The cancer treatment delivery method, cancer treatment delivery component, or method of forming a cancer treatment delivery component of any one of embodiments 1, 2, and 3, wherein the carbon-based nanomaterial composition comprises: a carbon content of at least about 75% and not greater than about 100% based on elemental analysis of the carbon-based nanomaterial composition, and an oxygen content of at least about 0.0% and not greater than about 25% based on elemental analysis of the carbon-based nanomaterial composition, wherein the carbon-based nanomaterial composition comprises a D/G ratio of at least about 0.1 and not greater than about 2.0; and wherein the carbon-based nanomaterial composition has a carbon hybridization ratio $P_{sp3}/P_{sp2}$ of at least about 0.0 and not greater than about 5.0, where $P_{sp3}$ is the percent of carbon within the carbon-based nanomaterial composition having a sp3 hybridization and $P_{sp2}$ is the percent of carbon within the carbon-based nanomaterial composition having a sp2 hybridization.

Embodiment 9. The cancer treatment delivery method, cancer treatment delivery component, or method of forming a cancer treatment delivery component of any one of embodiments 1, 2, and 3, wherein the carbon-based nanomaterial composition comprises: a carbon content of at least about 75% and not greater than about 100% based on elemental analysis of the carbon-based nanomaterial composition, and an oxygen content of at least about 0.0% and not greater than about 25% based on elemental analysis of the carbon-based nanomaterial composition, wherein the carbon-based nanomaterial composition comprises an aspect ratio at least about 1 and not greater than about 50; wherein the carbon-based nanomaterial composition has a carbon hybridization ratio $P_{sp3}/P_{sp2}$ of at least about 0.0 and not greater than about 5.0, where $P_{sp3}$ is the percent of carbon within the carbon-based nanomaterial composition having a sp3 hybridization and $P_{sp2}$ is the percent of carbon within the carbon-based nanomaterial composition having a sp2 hybridization.

Embodiment 10. The cancer treatment delivery method, cancer treatment delivery component, or method of forming a cancer treatment delivery component of any one of embodiments 1, 2, and 3, wherein the carbon-based nanomaterial composition comprises a carbon content of at least about 75% based on elemental analysis of the carbon-based nanomaterial composition.

Embodiment 11. The cancer treatment delivery method, cancer treatment delivery component, or method of forming a cancer treatment delivery component of any one of embodiments 1, 2, and 3, wherein the carbon-based nanomaterial composition comprises a carbon content of not greater than about 100% based on elemental analysis of the carbon-based nanomaterial composition.

Embodiment 12. The cancer treatment delivery method, cancer treatment delivery component, or method of forming a cancer treatment delivery component of any one of embodiments 1, 2, and 3, wherein the carbon-based nanomaterial composition comprises an oxygen content of at least about 0.0% based on elemental analysis of the carbon-based nanomaterial composition.

Embodiment 13. The cancer treatment delivery method, cancer treatment delivery component, or method of forming a cancer treatment delivery component of any one of embodiments 1, 2, and 3, wherein the carbon-based nanomaterial composition comprises an oxygen content of not greater than about 25.0% based on elemental analysis of the carbon-based nanomaterial composition.

Embodiment 14. The cancer treatment delivery method, cancer treatment delivery component, or method of forming a cancer treatment delivery component of any one of embodiments 1, 2, and 3, wherein the carbon-based nanomaterial composition comprises a carbon hybridization ratio $P_{sp3}/P_{sp2}$ of at least about 0.0, where $P_{sp3}$ is the percent of carbon within the carbon-based nanomaterial composition having a sp3 hybridization and $P_{sp2}$ is the percent of carbon within the carbon-based nanomaterial composition having a sp2 hybridization.

Embodiment 15. The cancer treatment delivery method, cancer treatment delivery component, or method of forming a cancer treatment delivery component of any one of embodiments 1, 2, and 3, wherein the carbon-based nanomaterial composition has a carbon hybridization ratio $P_{sp3}/P_{sp2}$ of not greater than about 5.0, where $P_{sp3}$ is the percent of carbon within the carbon-based nanomaterial composition having a sp3 hybridization and $P_{sp2}$ is the percent of carbon within the carbon-based nanomaterial composition having a sp2 hybridization.

Embodiment 16. The cancer treatment delivery method, cancer treatment delivery component, or method of forming a cancer treatment delivery component of any one of embodiments 1, 2, and 3, wherein the carbon-based nanomaterial composition comprises a D/G ratio of not greater than about 0.1.

Embodiment 17. The cancer treatment delivery method, cancer treatment delivery component, or method of forming a cancer treatment delivery component of any one of embodiments 1, 2, and 3, wherein the carbon-based nanomaterial composition comprises a D/G ratio of at least about 2.0.

Embodiment 18. The cancer treatment delivery method, cancer treatment delivery component, or method of forming a cancer treatment delivery component of any one of embodiments 1, 2, and 3, wherein the carbon-based nanomaterial composition comprises an aspect ratio of not greater than about 50.

Embodiment 19. The cancer treatment delivery method, cancer treatment delivery component, or method of forming a cancer treatment delivery component of any one of embodiments 1, 2, and 3, wherein the carbon-based nanomaterial composition comprises an aspect ratio of at least about 1.

Embodiment 20. The cancer treatment delivery method, cancer treatment delivery component, or method of forming a cancer treatment delivery component of any one of embodiments 1, 2, and 3, wherein the carbon-based nanomaterial composition is formed from a gas mixture.

Embodiment 21. The cancer treatment delivery method, cancer treatment delivery component, or method of forming a cancer treatment delivery component of any one of embodiments 1, 2, and 3, wherein the gas mixture comprises acetylene gas at a concentration of at least about 1.2 mol.

Embodiment 22. The cancer treatment delivery method, cancer treatment delivery component, or method of forming a cancer treatment delivery component of any one of embodiments 1, 2, and 3, wherein the gas mixture comprises acetylene gas at a concentration of not greater than about 18 mol.

Embodiment 23. The cancer treatment delivery method, cancer treatment delivery component, or method of forming a cancer treatment delivery component of any one of embodiments 1, 2, and 3, wherein the gas mixture comprises oxygen gas at a concentration of at least about 0.3 mol.

Embodiment 24. The cancer treatment delivery method, cancer treatment delivery component, or method of forming a cancer treatment delivery component of any one of embodiments 1, 2, and 3, wherein the gas mixture comprises oxygen gas at a concentration of not greater than about 12 mol.

Embodiment 25. The cancer treatment delivery method, cancer treatment delivery component, or method of forming a cancer treatment delivery component of any one of embodiments 1, 2, and 3, wherein the gas mixture comprises hydrogen gas at a concentration of at least about 0.6 mol.

Embodiment 26. The cancer treatment delivery method, cancer treatment delivery component, or method of forming a cancer treatment delivery component of any one of embodiments 1, 2, and 3, wherein the gas mixture comprises hydrogen gas at a concentration of not greater than about 20.0 mol.

Embodiment 27. The cancer treatment delivery method, cancer treatment delivery component, or method of forming a cancer treatment delivery component of any one of embodiments 1, 2, and 3, wherein the gas mixture comprises methane gas at a molar ratio $MG_{mol}/GM_{mol}$ of at least about 0.25 and not greater than about 0.99, where the $MG_{mol}$ is equal to the moles of methane gas in the gas mixture and $GM_{mol}$ is equal to the total moles of gas in the gas mixture.

Embodiment 28. The cancer treatment delivery method, cancer treatment delivery component, or method of forming a cancer treatment delivery component of any one of embodiments 1, 2, and 3, wherein the gas mixture comprises methane gas at a concentration of at least about 1.2 mol.

Embodiment 29. The cancer treatment delivery method, cancer treatment delivery component, or method of forming a cancer treatment delivery component of any one of embodiments 1, 2, and 3, wherein the gas mixture comprises methane gas at a concentration of not greater than about 18 mol.

Embodiment 30. The cancer treatment delivery method, cancer treatment delivery component, or method of forming a cancer treatment delivery component of any one of embodiments 1, 2, and 3, wherein the carbon-based nanomaterial composition is formed in a system for carbon-based nanomaterial composition synthesis, wherein the system comprises: an enclosed chamber comprising a hollow interior; a carbon-based gas source fluidically coupled to the chamber and configured to supply a carbon-based gas to the hollow interior; a hydrogen source that is independent of the carbon-based gas source and that is fluidically coupled to the chamber and configured to supply hydrogen to the hollow interior; an oxygen source that is independent of the carbon-based gas source and that is fluidically coupled to the chamber and configured to supply oxygen to the hollow interior; an igniter configured to ignite the carbon-based gas, hydrogen, and oxygen in the hollow interior; a first flow meter coupled to the carbon-based gas source, a second flow meter coupled to the hydrogen source, a third flow meter coupled to the oxygen source; and a controller in communication with and configured to receive flow data from the first, second, and third flow meters; wherein the controller is configured to adjust flow from one or more of the carbon-based gas source, the hydrogen source, and/or the oxygen source in response to the flow data.

Embodiment 31. The cancer treatment delivery method, cancer treatment delivery component, or method of forming a cancer treatment delivery component of embodiment 30, wherein the carbon-based gas is a flue gas resulting from an industrial reaction process.

Embodiment 32. The cancer treatment delivery method, cancer treatment delivery component, or method of forming a cancer treatment delivery component of embodiment 31, wherein the industrial reaction process is a coal energy plant, a drilling operation, a combustion engine, or a landfill.

Embodiment 33. The cancer treatment delivery method, cancer treatment delivery component, or method of forming a cancer treatment delivery component of embodiment 31, wherein the carbon-based gas source comprises a storage tank, an inlet line, and an outlet line; wherein the storage tank is coupled to the chamber via the outlet line; and wherein the flue gas is directed from the industrial reaction process through the inlet line to the storage tank.

Embodiment 34. The cancer treatment delivery method, cancer treatment delivery component, or method of forming a cancer treatment delivery component of embodiment 31, wherein the chamber is co-located with the industrial reaction process.

Embodiment 35. The cancer treatment delivery method, cancer treatment delivery component, or method of forming a cancer treatment delivery component of embodiment 30, further comprising an inert gas source fluidically coupled to the chamber and configured to supply an inert gas to the hollow interior.

Embodiment 36. The cancer treatment delivery method, cancer treatment delivery component, or method of forming a cancer treatment delivery component of embodiment 30, wherein the carbon-based gas source is coupled to the chamber via a first one-way valve, the hydrogen source is coupled to the chamber via a second one-way valve, and the oxygen source is coupled to the chamber via a third one-way valve.

Embodiment 37. The cancer treatment delivery method, cancer treatment delivery component, or method of forming a cancer treatment delivery component of embodiment 36, wherein the chamber further comprises an exhaust valve.

Embodiment 38. The cancer treatment delivery method, cancer treatment delivery component, or method of forming a cancer treatment delivery component of embodiment 30, further comprising a pressure sensor configured to measure a pressure within the hollow interior and a temperature sensor configured to measure a temperature within the hollow interior; wherein the controller is in communication with and configured to receive pressure data from the pressure sensor; wherein the controller is in communication with and configured to receive temperature data from the temperature sensor; and wherein the controller is configured to adjust flow from one or more of the carbon-based gas source, the hydrogen source, and the oxygen source in response to the flow data, the pressure data, the temperature data, or a combination thereof.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

The specification and illustrations of the embodiments described herein are intended to provide a general understanding of the structure of the various embodiments. The specification and illustrations are not intended to serve as an exhaustive and comprehensive description of all of the elements and features of apparatus and systems that use the structures or methods described herein. Separate embodiments may also be provided in combination in a single embodiment, and conversely, various features that are, for brevity, described in the context of a single embodiment, may also be provided separately or in any subcombination. Further, reference to values stated in ranges includes each and every value within that range. Many other embodiments may be apparent to skilled artisans only after reading this specification. Other embodiments may be used and derived from the disclosure, such that a structural substitution, logical substitution, or another change may be made without departing from the scope of the disclosure. Accordingly, the disclosure is to be regarded as illustrative rather than restrictive.

What is claimed is:

1. A cancer treatment delivery method comprising:
   preparing a cancer treatment delivery component comprising a carbon-based nanomaterial composition and a cancer treatment composition attached to the carbon-based nanomaterial composition;
   delivering the cancer treatment delivery component to a treatment location; and
   applying a radio frequency to the cancer treatment delivery component at the treatment location, wherein the radio frequency is configured to heat the cancer treatment delivery component and cause the cancer treatment composition to detach from the carbon-based nanomaterial composition for delivery at the treatment location, wherein the carbon-based nanomaterial composition comprises:

a carbon content of at least about 93 atomic percent (at. %) and not greater than about 97 at. % based on elemental analysis of the carbon-based nanomaterial composition conducted using x-ray photoelectron spectroscopy (XPS), and an oxygen content of at least about 1.0 at. % and not greater than about 2.5 at. % based on elemental analysis of the carbon-based nanomaterial composition conducted using XPS.

2. The cancer treatment delivery method of claim 1, wherein the cancer treatment composition comprises a cancer treatment, medicine or other molecule designed for delivery at a location within or on the surface of a body for cancer treatment or treatment at a location within or on the surface of a body for cancer treatment.

3. The cancer treatment delivery method of claim 1, wherein the treatment location comprises a cancer treatment, medicine or other molecule designed for delivery at a location within or on the surface of a body for cancer treatment or treatment at a location within or on the surface of a body for cancer treatment.

4. The cancer treatment delivery method of claim 1, wherein the radio frequency applied to the treatment location is at least about 100 MHz and not greater than about 140 Mhz.

5. The cancer treatment delivery method of claim 4, wherein the radio frequency is transmitted at a power of at least about 1 watt and not greater than about 5000 watts.

6. The cancer treatment delivery method of claim 4, wherein the radio frequency heats the treatment location to a temperature of at least about 50° C. and not greater than about 400° C.

7. The cancer treatment delivery method of claim 4, wherein the radio frequency is applied for a time length of at least about 0.01 seconds and not greater than about 60 seconds.

8. The cancer treatment delivery method of claim 1, wherein the carbon-based nanomaterial composition comprises a D/G ratio of at least about 0.1 and not greater than about 2.0; and wherein the carbon-based nanomaterial composition has a carbon hybridization ratio $P_{sp3}/P_{sp2}$ of at least about 0.1 and not greater than about 5.0, where $P_{sp3}$ is the percent of carbon within the carbon-based nanomaterial composition having a sp3 hybridization and $P_{sp2}$ is the percent of carbon within the carbon-based nanomaterial composition having a sp2 hybridization.

9. The cancer treatment delivery method of claim 1, wherein the carbon-based nanomaterial composition comprises an aspect ratio at least about 1 and not greater than about 50.

10. The cancer treatment delivery method of claim 1, wherein the carbon-based nanomaterial composition comprises a carbon hybridization ratio $P_{sp3}/P_{sp2}$ of at least about 0.1 and not greater than about 5.0, where $P_{sp3}$ is the percent of carbon within the carbon-based nanomaterial composition having a sp3 hybridization and $P_{sp2}$ is the percent of carbon within the carbon-based nanomaterial composition having a sp2 hybridization.

11. The cancer treatment delivery method of claim 1, wherein the carbon-based nanomaterial composition comprises a D/G ratio of not greater than about 0.1 and at least about 2.0.

12. A cancer treatment delivery component comprising:

a carbon-based nanomaterial composition and a cancer treatment composition attached to the carbon-based nanomaterial composition;

wherein the cancer treatment delivery component is configured to be delivered to a treatment location and heated using a radio frequency at the treatment location, wherein heating the cancer treatment delivery component causes the cancer treatment composition to detach from the carbon-based nanomaterial composition for delivery at the treatment location, wherein the carbon-based nanomaterial composition comprises:

a carbon content of at least about 93 at. % and not greater than about 97 at. % based on elemental analysis of the carbon-based nanomaterial graphene-composition, and an oxygen content of at least about 1.0 at. % and not greater than about 2.5 at. % based on elemental analysis of the carbon-based nanomaterial graphene-composition.

13. The cancer treatment delivery component of claim 12, wherein the cancer treatment composition comprises a cancer treatment, medicine or other molecule designed for delivery at a location within or on the surface of a body for cancer treatment or treatment at a location within or on the surface of a body for cancer treatment.

14. The cancer treatment delivery component of claim 12, wherein the treatment location comprises a cancer treatment, medicine or other molecule designed for delivery at a location within or on the surface of a body for cancer treatment or treatment at a location within or on the surface of a body for cancer treatment.

15. The cancer treatment delivery component of claim 12, wherein the radio frequency applied to the treatment location is at least about 100 MHz and not greater than about 140 Mhz.

16. The cancer treatment delivery component of claim 15, wherein the radio frequency is transmitted at a power of at least about 1 watt and not greater than about 5000 watts.

17. The cancer treatment delivery component of claim 15, wherein the radio frequency heats the treatment location to a temperature of at least about 50° C. and not greater than about 400° C.

18. The cancer treatment delivery component of claim 15, wherein the radio frequency is applied for a time length of at least about 0.01 seconds and not greater than about 60 seconds.

19. The cancer treatment delivery component of claim 12, wherein the carbon-based nanomaterial composition comprises a D/G ratio of at least about 0.1 and not greater than about 2.0; and wherein the carbon-based nanomaterial composition has a carbon hybridization ratio $P_{sp3}/P_{sp2}$ of at least about 0.1 and not greater than about 5.0, where $P_{sp3}$ is the percent of carbon within the carbon-based nanomaterial composition having a sp3 hybridization and $P_{sp2}$ is the percent of carbon within the carbon-based nanomaterial composition having a sp2 hybridization.

20. A method of forming a cancer treatment delivery component, wherein the method comprises:

providing a carbon-based nanomaterial composition, and attaching a cancer treatment composition to the carbon-based nanomaterial composition to form the cancer treatment delivery component, wherein the cancer treatment delivery component is configured to be delivered to a treatment location and heated using a radio frequency at the treatment location, wherein heating the cancer treatment delivery component causes the cancer treatment composition to detach from the carbon-based nanomaterial composition, wherein the carbon-based nanomaterial composition comprises:

a carbon content of at least about 93 at. % and not greater than about 97 at. % based on elemental analysis of the carbon-based nanomaterial graphene-composition conducted using XPS, and an oxygen content of at least about 1.0 at. % and not greater than about 2.5 at. % based on elemental analysis of the carbon-based nanomaterial graphene-composition conducted using XPS.

* * * * *